(12) United States Patent
Barrow et al.

(10) Patent No.: US 6,534,510 B2
(45) Date of Patent: Mar. 18, 2003

(54) THROMBIN INHIBITORS

(75) Inventors: James C. Barrow, Harleysville, PA (US); Bruce D. Dorsey, Maple Glen, PA (US); Harold G. Selnick, Ambler, PA (US); Phung L. Ngo, Upper Darby, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/815,404

(22) Filed: Mar. 22, 2001

(65) Prior Publication Data

US 2002/0006923 A1 Jan. 17, 2002

Related U.S. Application Data

(60) Provisional application No. 60/191,559, filed on Mar. 23, 2000.

(51) Int. Cl.[7] ............... C07D 401/00; A61K 31/495; A61K 31/50; A61K 31/535
(52) U.S. Cl. ............... 514/255.05; 544/405; 544/408
(58) Field of Search ............... 544/405, 408; 514/255.05

(56) References Cited

U.S. PATENT DOCUMENTS

| | | | |
|---|---|---|---|
| 5,260,307 A | 11/1993 | Ackermann et al. | 514/323 |
| 5,405,854 A | 4/1995 | Ackermann et al. | 514/315 |
| 5,455,348 A | 10/1995 | Austel et al. | 544/238 |
| 5,459,142 A | 10/1995 | Tone et al. | 514/252 |
| 5,510,369 A | 4/1996 | Lumma et al. | 514/422 |
| 5,744,486 A | 4/1998 | Sanderson et al. | 514/318 |
| 5,866,573 A | 2/1999 | Sanderson et al. | 514/235.8 |
| 5,981,546 A | 11/1999 | Duggan et al. | 514/300 |
| 6,180,627 B1 | 1/2001 | Blagg et al. | 514/235.8 |

FOREIGN PATENT DOCUMENTS

| | | |
|---|---|---|
| EP | 0 262 096 A1 | 9/1987 |
| EP | 0 509 769 A2 | 4/1992 |
| EP | 0 997 474 A1 | 5/2000 |
| WO | WO 94/25051 | 11/1994 |
| WO | WO 96/11697 | 4/1996 |
| WO | WO 96/31504 | 10/1996 |
| WO | WO 96/32110 | 10/1996 |
| WO | WO 97/01338 | 1/1997 |
| WO | WO 97/40024 | 10/1997 |
| WO | WO 98/47876 | 10/1998 |
| WO | WO 99/11267 | 3/1999 |

OTHER PUBLICATIONS

Rauch et al., PubMed Abstract (Ann. Intern. Med., 134(3): 224–38), Feb. 2001.*
Van Aken et al., PubMed Abstract (Clin. Appl. Thromb. Hemost., 7(3): 195–204) Jul. 2001.*
Peter R. Berstein, et al., "Nonpeptidic Inhibitors of Human Leukocyte Elastase . . . " *J. Med. Chem.*, vol. 37, 1994, pp. 3313–3326.
Sanderson, et al., "Preparation of 3–amino–2–pyrazinone–1–acetamide derivatives as thrombin inhibitors," *Chem. Abstracts* (The Amer. Chem. Soc.), vol. 128, No. 3, pp. 532–533, 22922r, Jan. 19, 1998.
Kitazawa, et al., "Preparation of 1,4–disubstituted cyclic amino derivatives as sertonin antagonists," Database CA on Stn., Document No. 129:302552, Abstract, WO 98 43956, (1998).

* cited by examiner

*Primary Examiner*—Deepak Rao
(74) *Attorney, Agent, or Firm*—Richard S. Parr; Melvin Winokur; Valerie J. Camara

(57) ABSTRACT

Compounds of the invention are useful in inhibiting thrombin and associated thrombotic occlusions and are selected from the group consisting of:

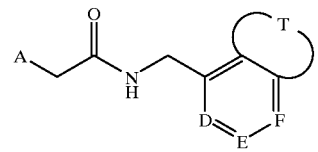

or a pharmaceutically acceptable salt thereof, wherein A is

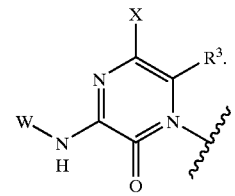

7 Claims, No Drawings

THROMBIN INHIBITORS

CROSS-REFERENCE TO RELATED APPLICATION

This application claims priority to provisional application number 60/191,559, filed Mar. 23, 2000.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.*, (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., *J. Med. Chem.*, Vol. 37, pages 1259–1261 (1994) describes orally active, non-peptidic inhibitors of human leukocyte elastase which contain trifluoromethylketone and pyridinone moieties.

H. Mack et al., *J. Enzyme Inhibition*, Vol. 9, pages 73–86 (1995) describes rigid amidino-phenylalanine thrombin inhibitors which contain a pyridinone moiety as a central core structure.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions. The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

The invention is a compound selected from the group consisting of:

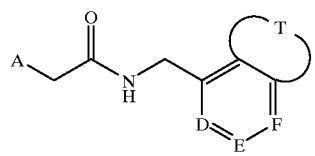

or a pharmaceutically acceptable salt thereof, wherein
T is selected from the group consisting of

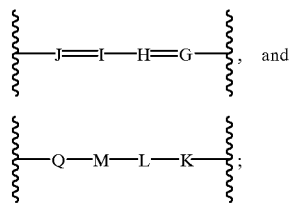

D, E, F, G, H, I, and J are independently N or $CY^1$ provided that the number of such variables D, E, F, G, H, I, and J representing N is 0, 1, or 2;

K, L, M and Q are independently NH or $CY^1Y^2$, provided that the number of such variables D, E, F, K, L, M, and Q representing N is 0, 1, or 2;

$Y^1$ and $Y^2$ are independently selected from the group consisting of hydrogen,
$C_{1-4}$alkyl,
halogen,
amino, or
hydroxy;

A is

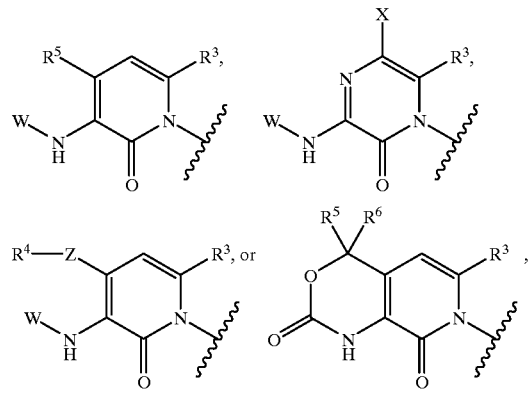

W is
hydrogen
$R^1$,
$R^1OCO$,
$R^1CO$,
$R^1SO_2$,
$R^1(CH_2)_nNHCO$,
wherein n is 0–4;
$R^1$ is
$R^2$,
$R^2(CH_2)_mC(R^{12})_2$, where m is 0–3, and each $R^{12}$ can be the same or different, $(R^2)(OR^2)CH(CH_2)_p$, where p is 1–4,

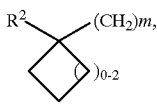

where m is 0–3, $R^2C(R^{12})_2(CH_2)_m$, wherein m is 0–3, and each $R^{12}$ can be the same or different, wherein $(R^{12})_2$ can also form a ring with C represented by $C_{3-7}$ cycloalkyl, $R^2CH_2C(R^{12})_2(CH_2)_q$, wherein q is 0–2, and each $R^{12}$ can be the same or different, wherein $(R^{12})_2$ can also form a ring with C represented by $C_{3-7}$ cycloalkyl, $(R^2)_2CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicylic alkyl, $C_{10-16}$ tricyclic alkyl, or a 5- to 7-membered mono- or bicyclic heterocyclic ring which can be saturated or unsaturated, and which contains from one to three heteroatoms selected from the group consisting of N, O and S, $R^2(CH_2)_tO(CH_2)_p$, wherein t is 0 or 1 and p is 1–4, $R^2CF_2C(R^{12})_2$, $(R^2CH_2)(R^2CH_2)N-$, $(R^2CH_2)(R^2CH_2)CH$, or $R^2(COOR^3)(CH_2)_r$, where r is 1–4;

$R^2$ and $R^4$ are independently phenyl, unsubstituted or substituted with one or more of $C_{1-4}$ alkyl, $C_{1-4}$ alkoxy, halogen, hydroxy, COOH, $CONH_2$, $CH_2H$, $CO_2R'$, where R' is $C_{1-4}$ alkyl, or $SO_2NH_2$, naphthyl, biphenyl, pyridine N-oxide, a 5- to 7-membered mono- or a 9- to 10-membered bicyclic
  a) non-heterocyclic ring system, which is saturated or unsaturated, and which is unsubstituted or substituted with halogen or hydroxy, or
  b) heterocyclic ring system, which is saturated or unsaturated, having carbon ring atoms and heteroatom ring atoms, wherein the ring system contains i) from one to four heteroatoms selected from the group consisting of N, O, and S, and wherein the ring system is unsubstituted, or ii) from one to four nitrogen atoms, wherein one or more of the carbon and nitrogen ring atoms are substituted with halogen or hydroxy.

$C_{1-7}$ alkyl, unsubstituted or substituted with one or more of hydroxy,
  COOH,
  amino,
  aryl,
  $C_{3-7}$ cycloalkyl,
  $CF_3$,
  $N(CH_3)_2$,
  $-C_{1-3}$alkylaryl,
  heteroaryl, or
  heterocycloalkyl, $CF_3$ $C_{3-7}$ cycloalkyl, unsubstituted or substituted with aryl, $C_{7-12}$ bicyclic alky, or $C_{10-16}$ tricyclic alkyl;

$R^3$, $R^5$ and $R^6$ are independently selected from the group consisting of
  hydrogen,
  halogen,
  $C_{1-4}$ alkyl,
  $C_{3-7}$ cycloalkyl, or
  trifluoromethyl;

X is
  hydrogen, or
  halogen;

Z is $CH_2$, S, or $SO_2$;

$R^{12}$ is hydrogen, phenyl, unsubstituted or substituted with one or more of $C_{1-4}$ alkyl, $C_{1-4}$ alkoxy, halogen, hydroxy, COOH, $CONH_2$, naphthyl, biphenyl, a 5- to 7-membered mono- or a 9- to 10-membered bicyclic heterocyclic ring which can be saturated or unsaturated, and which contains from one to four heteroatoms selected from the group consisting of N, O and S, $C_{1-4}$ alkyl, unsubstituted or substituted with one or more of hydroxy,
  OH,
  COOH,
  amino,
  $-N(CH_3)_2$,
  $-NH(CH_3)$,
  $-N(CH_2)COOH$,
  aryl,
  heteroaryl, or
  heterocycloalkyl, $CF_3$ $C_{3-7}$ cycloalkyl, $C_{7-12}$ bicyclic alkyl, or $C_{10-16}$ tricyclic alkyl.

In one class of compounds of the invention, $Y^1$ and $Y^2$ are hydrogen or amino. In a subclass of this class of compounds, A is

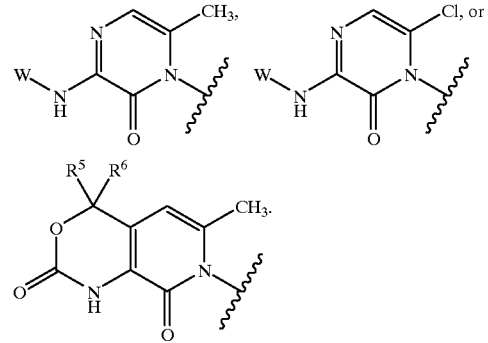

In a group of this subclass, $R^5$ and $R^6$ are independently selected from $-CH(CH_3)_2$ and $-CH_2CH_3$, and W is selected from the group consisting of:

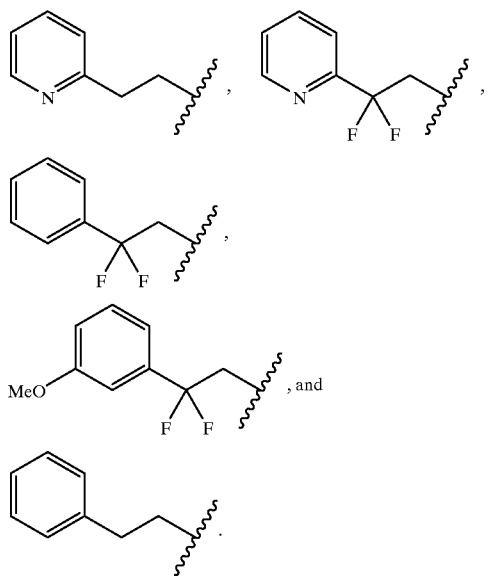
Examples of this group are listed below. Inhibitory activity of compounds of the invention is represented by "**" indicating Ki greater than or equal to 20 nM, or "*", indicating Ki less than 20 nM. Values are as determined according to the in vitro assay described later in the specification.
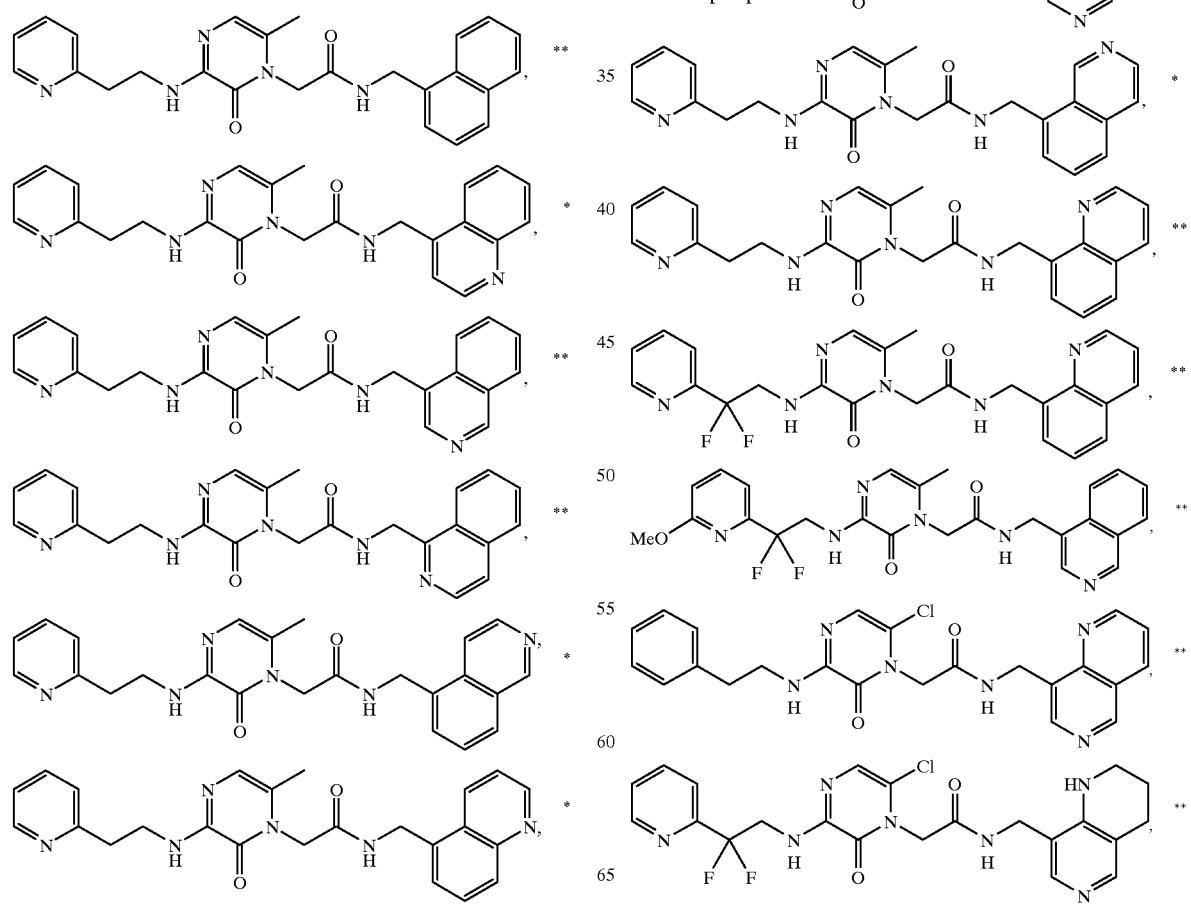

-continued

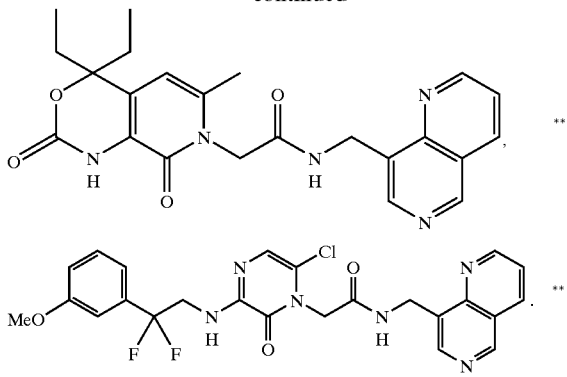

The term "alkyl" means branched or straight-chain saturated aliphatic hydrocarbon groups having the specified number of carbon atoms (for example, "$C_{1-10}$" denotes alkyl having 1 to 10 carbon atoms, e.g., methyl, ethyl, n-propyl, isopropyl, n-butyl, isobutyl, sec-butyl, tert-butyl, pentyl, iso-amyl, hexy, octyl radicals and the like.

The term "alkenyl" means hydrocarbon chains of either a straight of branched configuration and one or more unsaturated carbon—carbon bonds which may occur at an stable point along the chain, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like.

The term, "alkynyl" means hydrocarbon chains of either a straight or branched configuration and one or more triple carbon-carbon bonds which may occur in any stable point along the chain, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alkoxy" means an alkyl group of indicated number of carbon atoms attached through an oxygen bridge, e.g., methoxy, ethoxy, n-propoxy, isopropoxy, n-butoxy, isobutoxy, sec-butoxy, tert-butoxy, pentyloxy, radicals and the like.

The terms "alkylene", "alkenylene", "phenylene", and the like, refer to alkyl, alkenyl, and phenyl groups, respectively, which are connected by two bonds to the rest of the structure. Such "alkylene", "alkenylene", "phenylene", and the like, may alternatively and equivalently be denoted herein as "—(alkyl)—", "—(alkenyl)—" and "—(phenyl)—", and the like.

The term "halogen" includes fluorine, chlorine, iodine and bromine.

The term "oxy" means an oxygen (O) atom.
The term "thio" means a sulfur (S) atom.
The term "aryl" means a partially saturated or fully saturated 6–14 membered ring system such as for example, phenyl, naphthyl or anthracyl. The term "Ph", which appears in certain chemical formulas in the specification and claims, represents phenyl.

The term "cycloalkyl" means saturated ring groups, including mono-, bi-, or poly-cyclic ring systems such as cyclopropyl, cyclobutyl, cyclopentyl, cyclohexy, cycloheptyl, cyclooctyl, adamantyl, and the like.

The term "heterocyclic" or "heterocycle" means a stable 5- to 7-membered monocyclic or bicyclic or 7- to 10-membered bicyclic heterocyclic ring which may be saturated, partially unsaturated, or fully unsaturated, which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of heterocyclic rings include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxanthiinyl, 2H-pyrrolyl, pyrrolyl, imidazolyl, pyrazolyl, isothiazolyl, isoxazolyl, oxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl or oxazolidinyl. Also included are fused ring and spiro compounds containing, for example, the above heterocycles.

The term "heteroaryl" means an unsaturated heterocyclic group, preferably 5 or 6-membered monocyclic ring systems or 8–10 membered fused bicyclic groups, having heteroatoms selected from the group consisting of N, O, and S, for example, pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyridazinyl, benzofuranyl, benzothienyl, benzimidazolyl, quinolinyl, or isoquinolinyl.

Under standard nonmenclature used throughout this disclosure, the terminal portion of the designated side chain is described first followed by the adjacent functionality toward the point of attachment. For example, a methylene substituted with ethylcarbonylamino is equivalent to

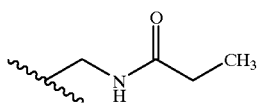

Compounds of the present invention may be chiral; included within the scope of the present invention are racemic mixtures and separated enantiomers of the general formula. Furthermore, all diastereomers, including E, Z isomers, of the general formula are included in the present scope. Furthermore, hydrates as well as anhydrous compositions and polymorphs of the general formula are within the present invention. Thus, the term "active drug" includes a compound of the invention and its salts, racemic mixtures or separated enantiomers, hydrates or anhydrous forms, polymorphs, and pharmaceutically acceptable salts.

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Prodrugs, such as ester derivatives of active drug are compound derivatives which, when absorbed into the bloodstream of a warm-blooded animal, cleave in such a manner as to release the drug form and permit the drug to afford improved therapeutic efficacy.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

Some abbreviations that may appear in this application are as follows.

| ABBREVIATIONS | |
| --- | --- |
| Designation | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| Activating Group | |
| HBT(HOBT or HOBt) | 1-hydroxybenzotriazole hydrate |
| Designation | Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chloric |
| EDC | 1-ethyl-3-(3-dimethylaminopropyl) carbodiimide hydrochloride |
| | Other |
| $(BOC)_2O(BOC_2O)$ | di-t-butyl dicarbonate |
| n-Bu$_4$N + F- | tetrabutyl ammonium fluoride |
| nBuLi (n-Buli) | n-butyllithium |
| DMF | dimethylformamide |
| Et$_3$N (TEA) | triethylamine |
| EtOAc | ethyl acetate |
| TFA | trifluoroacetic acid |
| DMAP | dimethylaminopyridine |
| DME | dimethoxyethane |
| NMM | N-methylmorpholine |
| DPPA | diphenylphosphoryl azide |
| THF | tetrahydrofuran |
| DIPEA | diisopropylethylamine |
| | Amino Acid |
| Ile | Isoleucine |
| Phe | Phenylalanine |
| Pro | Proline |
| Ala | Alanine |
| Val | Valine |

IN VITRO ASSAY FOR DETERMINING PROTEINASE INHIBITION

Assays of human a-thrombin and human trypsin were performed by the methods substantially as described in *Thrombosis Research*, Issue No. 70, page 173 (1993) by S. D. Lewis et al.

The assays were carried out at 25° C. in 0.05 M TRIS buffer pH 7.4, 0.15 M NaCl, 0.1% PEG. Trypsin assays also contained 1 mM $CaCl_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human a-thrombin ($K_m$=125 μM) and bovine trypsin ($K^m$=125 μM). p-Nitroanilide substrate concentration was determined from measurements of absorbance at 342 nm using an extinction coefficient of 8270 $cm^{-1}M^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration $\leq 0.1$ $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in equation 1.

$$V_o/V_i = 1 + [I]/K_i \qquad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. The compounds of the invention are selective compounds, as evidenced by their inhibitory activity against human trypsin (represented by Ki), which is at least 1000 nM.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems.

The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Coming Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethylaspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Typical uncoated tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

Schemes A through I outline general procedures for making intermediates having the general formula

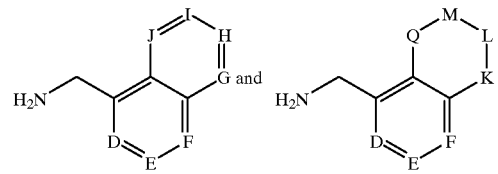

Scheme A

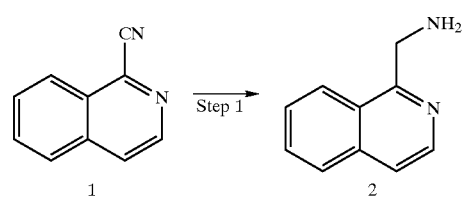

Scheme B
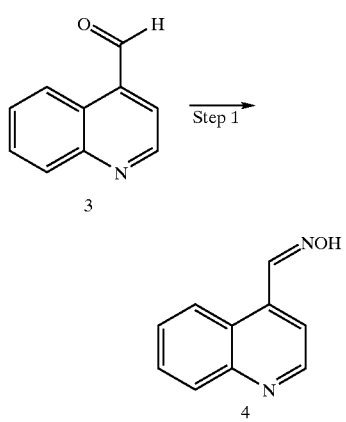
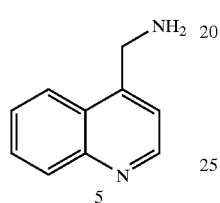
Scheme C
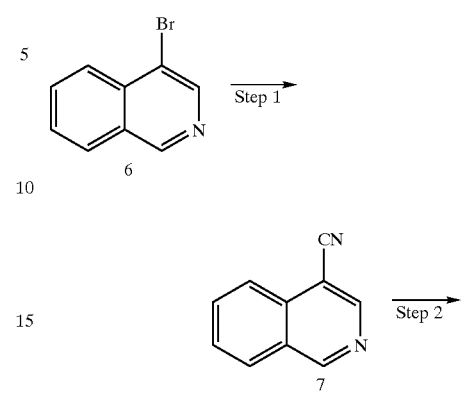
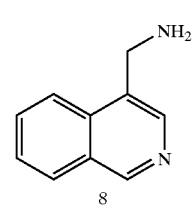
Scheme D
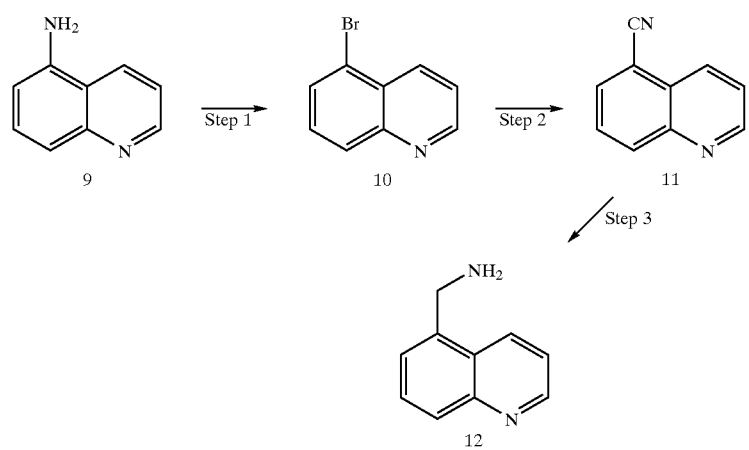
Scheme E
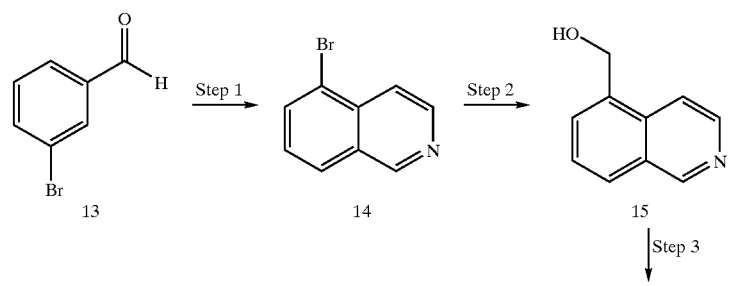

-continued
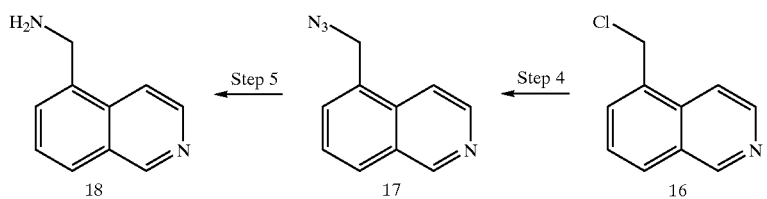
Scheme F
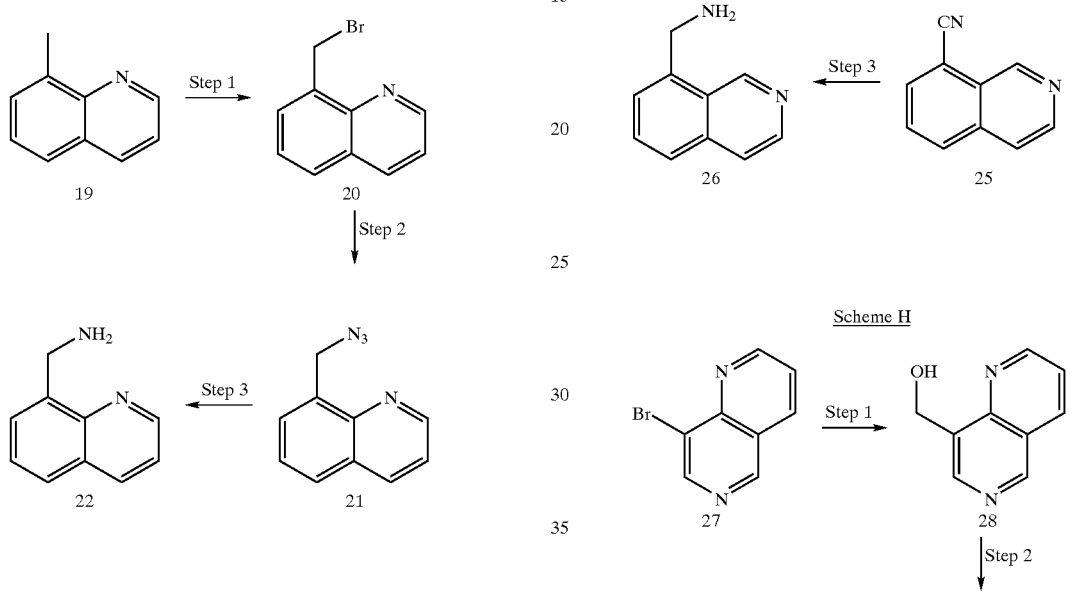
Scheme G
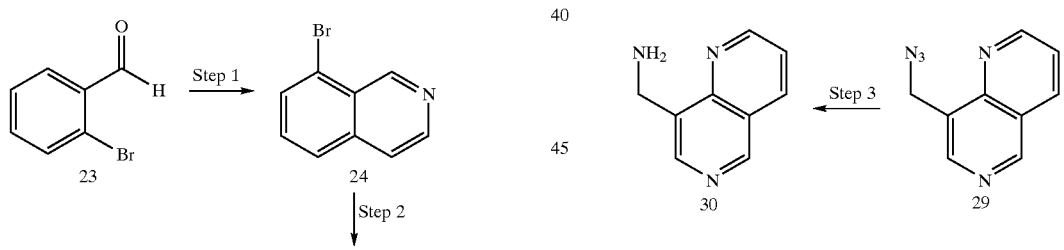
Scheme H
Scheme I
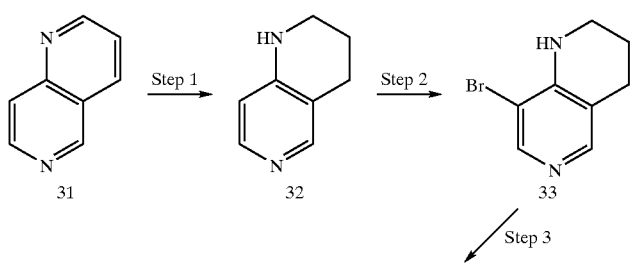

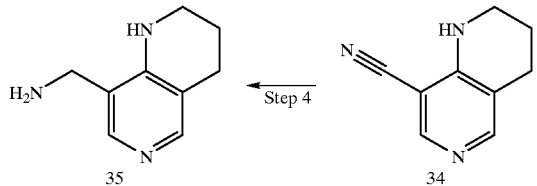

General Procedure for Making Compounds of the Invention

Compounds may be prepared, for example, by a common condensation reaction between a group having a carboxylic acid moiety and a group having an amino moiety, forming a peptide or amide bond. Compounds may be prepared by other means however, and suggested starting materials and procedures described below are exemplary only and should not be construed as limiting the scope of the invention.

In general, compounds having the general structure

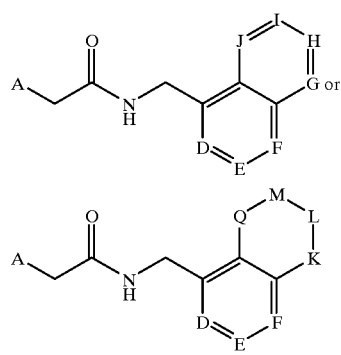

wherein the variables have the above-described meanings, can be prepared by reacting

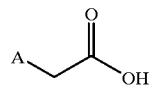

with an amino-containing intermediate selected from the group consisting of

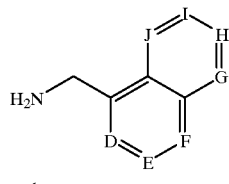

and

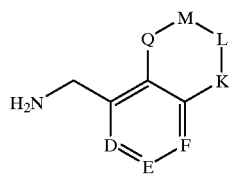

under conditions suitable for forming an amide bond between the acid and the amine.

Suitable carboxylic acid starting materials for

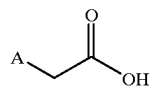

may be prepared according to the following procedures.

Carboxylic Acids

METHOD 1

Starting allylamine is condensed with acetaldehyde and cyanide in Step A to afford the aminonitrile. This is reacted in Step B with oxalyl chloride according to the method of Hoomaert [*J. Heterocyclic Chem.*, 20, 919, (1983)] to give the pyrazinone. The olefin is oxidatively cleaved with ruthenium tetraoxide and the resulting aldehyde is converted to the acid by an oxidizing agent such as chromic acid in Step C. The 3-chloro group is then displaced by an ammonia equivalent, in this case p-methoxybenzylamine in Step D. The remaining chlorine is removed by reduction with Raney nickel in Step E and in Step F the p-methoxybenzyl group is removed by treatment with a strong acid such as TFA.

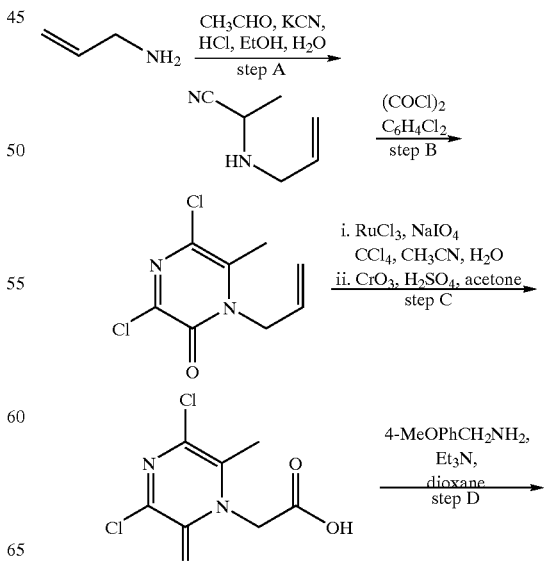

-continued

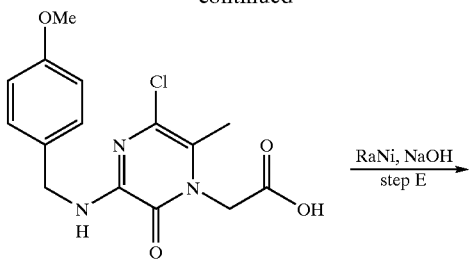

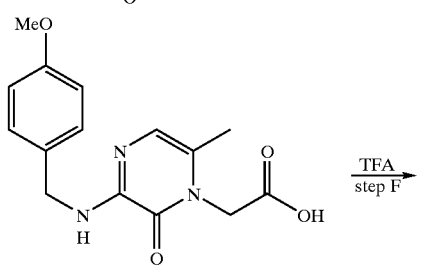

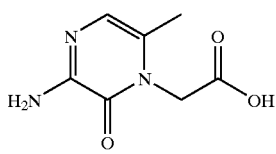

Typically, solution phase amide couplings may be used to form the final product, but solid-phase synthesis by classical Merrifield techniques may be employed instead. The addition and removal of one or more protecting groups is also typical practice.

Modifications of the method will allow different W, $R^3$, and X groups contemplated by the scope of the broad claim below to be present by the use of an appropriate reagent or appropriately substituted starting material in the indicated synthetic step. For example the starting aldehyde in Step A can have as its side chain, ethyl, isopropyl, cyclopropyl, trifluoromethyl, and the like, to achieve the different operable values of $R^3$. Likewise, different W groups can be present by the use of an appropriate amine in Step D. Different X groups can be present by the omission of step E, and by the use of a reagent such as oxalyl bromide in step B. Obvious variations and modifications of the method to produce similar and obvious variants thereof, will be apparent to one skilled in the art.

METHOD 2

The acid from METHOD 1, Step C is coupled to the appropriate amine. The 3-chloro group is then displaced by the appropriate amine and a protecting group is then removed, if necessary, to give the final product.

Modifications of the method will allow different W, $R^3$, and X groups contemplated by the scope of the broad claim below to be present by the use of an appropriate reagent or appropriately substituted starting material in the indicated synthetic step. Obvious variations and modifications of the method to produce similar and obvious variants thereof, will be apparent to one skilled in the art.

METHOD 3

An ester of glycine, in this case the benzyl ester, is condensed with acetaldehyde and cyanide in Step A to afford the aminonitrile. This is reacted in Step B with oxalyl chloride to give the pyrazinone. The 3-chloro group is then displaced by the appropriate amine, in this case phenethylamine, in Step C. The ester is hydrolyzed in Step D and the remaining chlorine is then removed by hydrogenolysis in Step E.

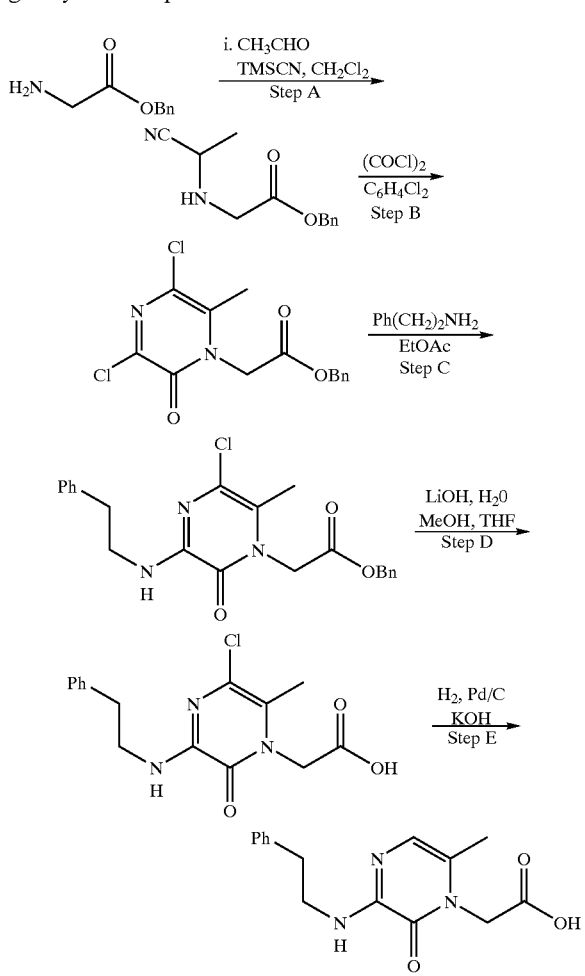

METHOD 4

Starting allylamine is condensed with acetaldehyde and cyanide in Step A to afford the aminonitrile. This is reacted in Step B with oxalyl chloride according to the method of Hoornaert [*J. Heterocyclic Chem.*, 20, 919, (1983)] to give the pyrazinone. The olefin is oxidatively cleaved with ruthenium tetraoxide and the resulting aldehyde is converted to the acid by an oxidizing agent such as chromic acid in Step C. The 3-chloro group is then displaced by the appropriate amine, in this case phenethylamine, in Step D and the remaining chlorine is then removed by reduction with Raney nickel in Step E.

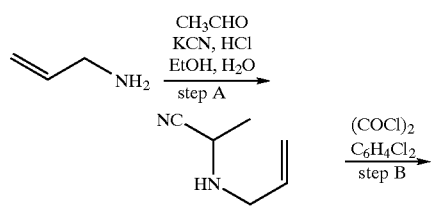

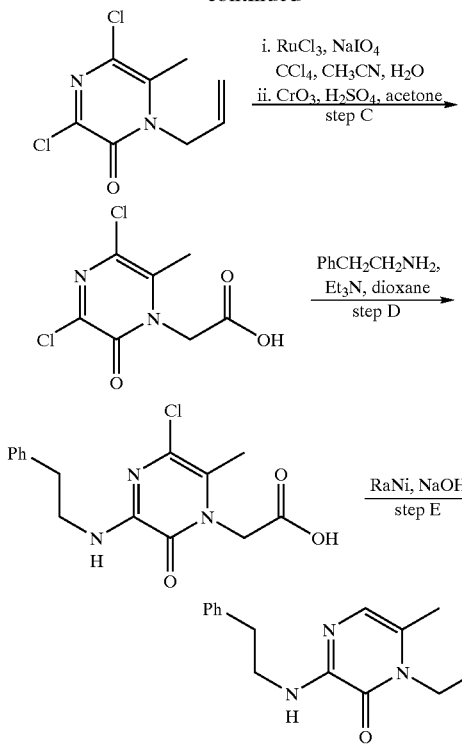

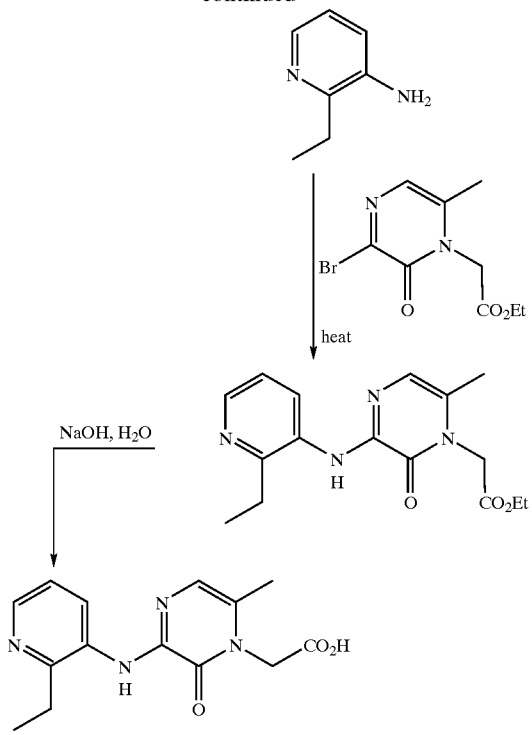

Amide couplings to form the compounds of this invention can be performed by the carbodiimide method. Other methods of forming the amide or peptide bond include, but are not limited to the synthetic routes via an acid chloride, azide, mixed anhydride or activated ester. Typically, solution phase amide couplings are performed, but solid-phase synthesis by classical Merrifield techniques may be employed instead. The addition and removal of one or more protecting groups is also typical practice.

Modifications of the method will allow different W, $R^3$, and X groups contemplated by the scope of the broad claim below to be present by the use of an appropriate reagent or appropriately substituted starting material in the indicated synthetic step. For example the starting aldehyde in Step A can have as its side chain, ethyl, isopropyl, cyclopropyl, trifluoromethyl, and the like, to achieve the different operable values of $R^3$. Likewise, different W groups can be present by the use of an appropriate amine in Step D. Different X groups can be present by the omission of step E, and by the use of a reagent such as oxalyl bromide in step B. Obvious variations and modifications of the method to produce similar and obvious variants thereof, will be apparent to one skilled in the art.

METHOD 5

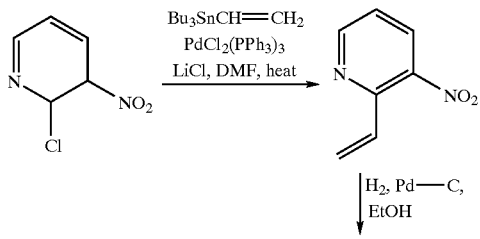

METHOD 6

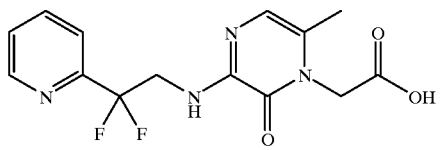

Ethyl 2-pyridinoylformate (6-1).

To a stirred solution of 20 mL (210 mmol) of 2-bromopyridine in 500 mL of dry ether at −78° C. under Ar was added 85 mL of a 2.5 M solution of n-butyllithium in hexane in a slow stream. After stirring in the cold for 30 min, the solution was transferred over a 5 min period via two cannula into a 0° C. stirred solution of 100 mL (736 mmol) of diethyl oxalate in 1.0 L of dry ether under Ar. After stirring for 2 h in the cold, the reaction mixture was washed with 600 mL of sat. NaHCO$_3$, water, and brine. The solution was dried over MgSO$_4$ and the solvents concentrated at reduced pressure to give a red oil that was purified by SiO$_2$ chromatography (10×15 cm) using 1:4 to 35:65 EtOAc-hexanes. The product-containing fractions were concentrated at reduced pressure to afford 6-1 as a reddish oil: $^1$H NMR (CDCl$_3$) δ 1.42 (t, 3H), 4.45–4.55 (m, 2H), 7.55–7.6 (m, 1H), 7.9–7.95 (m, 1H), 8.11 (d, 1H), 8.78 (d, 1H).

Ethyl difluoro-2-pyridylacetate (6-2).

A stirred solution of 22 g (123 mmol) of ethyl 2-pyridinoylformate 6-1 and 75 g (465 mmol) of diethylaminosulfurtrifluoride (DAST) were heated to 55° C. under Ar overnight. Because the reaction was not complete, 5 g additional DAST was added, and the reaction heated for an additional 24 h. The reaction mixture was cooled to rt, and poured very slowly into a stirred mixture of 1 kg of ice, 400 mL of ethyl acetate and 500 mL of sat. NaHCO$_3$. After the addition, the mixture was basified by the addition of solid NaHCO$_3$. The aqueous layer was extracted with EtOAc, and the combined organic layers washed with sat. NaHCO$_3$, brine, dried over Na$_2$SO$_4$ and the solvents concentrated at reduced pressure to give 6-2 as a brown oil: $^1$H NMR (CDCl$_3$) δ1.35 (t, 3H), 4.35–4.4 (m, 2H), 7.4–7.45 (m, 1H), 7.75 (d, 1H), 7.95 (d, 1H), 8.45 (d, 1H).

2,2-Difluoro-2-(2-pyridyl)ethanol (6-3).

To a stirred solution of 19.5 g (97 mmol) of ethyl difluoro-2-pyridylacetate 6-2 in 200 mL of absolute ethanol at 0° C. was added 4.42 g (116 mmol) of sodium borohydride in small portions. After 30 min, the reaction was quenched by the addition of 50 mL of sat. NH$_4$Cl. The reaction mixture was concentrated at reduced pressure and the residue partitioned between 500 mL of ethyl acetate and sat. NaHCO$_3$. The organic layer was washed with water, brine, and dried over Na$_2$SO$_4$ and concentrated at reduced pressure to give a brown oil that was purified on SiO$_2$ (10×17 cm) using 1:1 EtOAc-hexane. After re-chromatographing the mixed fractions, all clean fractions were combined and concentrated at reduced pressure, giving 6-3 as a beige crystalline solid: $^1$H NMR (CDCl$_3$) δ 3.6 (t, 1H), 4.17–4.3 (m, 2H), 7.4–7.45 (m, 1H), 7.73 (d, 1H), 7.84–7.91 (m, 1H ), 8.61 (d, 1H).

2,2-Difluoro-2-(2-pyridyl)ethyl trifluoromethanesulfonate (6-4).

To a stirred solution of 5 g (31.4 mmol) of 2,2-difluoro-2-(2-pyridyl)ethanol 6-3 and 9.69 g (47.2 mmol) of 2,6-di-t-butyl-4-methylpyridine in 110 mL of methylene chloride at −78° C. under Ar was added 7.93 mL (47.2 mmol) of triflic anhydride dropwise. After 1 h, the reaction was diluted with 100 mL of pentane and filtered. The filtrate was concentrated and treated again with pentane and filtered. Concentration of the filtrate gave 6-4 as a brown oil, contaminated with 2,6-di-t-butyl-4-methylpyridine: $^1$H NMR (CDCl$_3$) δ 5.12 (t, 2H), 7.45–7.5 (m, 1H), 7.75 (d, 1H), 7.86–7.94 (m, 1H), 8.65 (d, 1H).

2,2-Difluoro-2-(2-pyridyl)ethylazide (6-5).

To a stirred solution of 5.5 g of 2,2-difluoro-2-(2-pyridyl) ethyl trifluoromethanesulfonate 6-4 in 70 mL of DMF was added 6.74 g (104 mmol) of sodium azide under Ar. The mixture was heated to 60° C. overnight. A second batch was run in the same manner, and after cooling to rt, both reactions were poured into 600 mL of water, and extracted with 3×500 mL of ether. The combined extracts were washed with brine, dried over Na$_2$SO$_4$ and concentrated at reduced pressure to give an oil that was purified by SiO$_2$ (10×6 cm) using hexane 1:3 EtOAc-hexane and 1:1 EtOAc-hexane. The product-containing fractions were concentrated at reduced pressure to give 6-5 as a yellow oil: $^1$H NMR (CDCl$_3$) δ 4.05 (t, 2H), 7.4–7.45 (m, 1H), 7.73 (d, 1H), 7.83–7.89 (m, 1H), 8.67 (d, 1H).

2,2-Difluoro-2-(2-pyridyl)ethylamine (6—6).

A stirred solution of 100 mg of 2,2-difluoro-2-(2-pyridyl) ethylazide 6—6 was hydrogenated in 10 mL of ethyl acetate over 100 mg of 10% palladium on carbon using a balloon for 1 h. The catalyst was removed by filtration and the solvents removed at reduced pressure. A total of 1.8 g (9.7 mmol) of the azide was reduced using this procedure to give 6—6 as a yellow oil: $^1$H NMR (CDCl$_3$) 67 8.66 (d, 1H, 4.2 Hz), 7.82 (td, 1H, 7.7, 1.7 Hz), 7.68 (d, 1H, 8.1 Hz), 7.37–7.40 (m, 1H), 3.44 (t, 2H, 14.3 Hz), 1.41 (br s, 2H).

Ethyl 3-(2,2-difluoro-2-(2-pyridylethylamino)-6-methylpyrazin(1H)-2-one-1-acetate (6-7). A solution of 7.13 g (45.1 mmol) of 2,2-difluoro-2-(2-pyridyl)ethylamine and 12.4 g (45.1 mmol) of ethyl 3-bromo-6-methylpyrazin(1H)-2-one-1-acetate was heated to 125° C. in a sealed tube overnight in 15 mL of toluene and 15 mL of ethanol. The reaction was concentrated and the residue was diluted with ethyl acetate, washed with 15% NaHCO$_3$ and the aqueous layer backwashed with 3 portions of ethyl acetate. The combined organic layers were dried over MgSO$_4$ and the solvents removed at reduced pressure to give an oil that was chromatographed on SiO$_2$ using 50:50 hexane-EtOAc to give the title compound as a pale yellow solid: $^1$H NMR (CDCl$_3$) δ 8.67 (d, 1H, 4.8 Hz), 7.80 (t, 1H, 7.9 Hz), 7.68 (d, 1H, 7.9 Hz), 7.36–7.39 (m, 1H), 6.71 (s, 1H), 6.31 (br t, 1H), 4.69 (s, 2H), 4.35 (td, 2H, 14.1, 6.6 Hz), 4.24 (q, 2H, 7.1 Hz), 2.11 (s, 3H), 1.29 (t, 3 H, 6.8 Hz).

3-(2,2-Difluoro-2-(2-pyridylethylamino)-6-methylpyrazin(1H)-2-one-1-acetic acid (6-8).

To a stirred solution of 9.67 g (27.5 mmol) of ethyl 3-(2,2-difluoro-2-(2-pyridylethylamino)-6-methylpyrazin(1H)-2-one-1-acetate in 100 mL of methanol was added 8.58 g (153.0 mmol) of potassium hydroxide in 20 mL of water. After 1 h, the solution was concentrated at reduced pressure, and the residue dissolved in 25 mL of water. This solution was acidified to pH=7 using 1.3 M HCl, and concentrated at reduced pressure to give a yellow solid containing potassium chloride and the title compound: $^1$H NMR (CD$_3$OD) 67 8.65 (d, 1H, 4.7 Hz), 7.95 (td, 1H, 7.9, 1.8 Hz), 7.72–7.74 (m, 1H), 7.50–7.54 (m, 1H), 6.64 (d, 1H, 1.09 Hz), 4.78 (s, 2H), 4.31 (t, 2H, 14.1 Hz), 2.16 (s, 3H).

METHOD 7

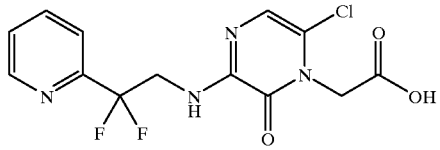

Ethyl N-(ethyl carboxymethyl)oxamate (7-1)

To a suspension of ethyl glycine•HCl (38.4 g, 275 mmol) in 1,2-dichloroethane (360 mL) was added triethylamine (77.0 mL, 550 mmol) at room temperature. After stirring for 30 minutes the heterogenous mixture was cooled to 0° C. and ethyl oxalyl chloride (30.3 mL, 275 mol) was added dropwise over the course of 1 h. Upon completion of the addition, the cooling bath was removed and the reaction was stirred at room temperature overnight. The reaction was diluted with water (250 mL) and the layers separated. The aqueous layer was backwashed with 2 portions of dichloromethane (250 mL). The combined organic layers were washed with water (250 mL), followed by brine (250 mL), dried over MgSO$_4$ and concentrated to give an oil 7-1 that was taken directly onto the next step.

N-(Ethyl carboxymethyl)-N'-(2,2-dimethoxyethyl)oxamide (7-2)

To a solution of the oxamate (84.0 g, 414 mmol) 7-1 in 2-propanol (500 mL) was added aminoacetaldehyde dimethyl acetal (45.7 g, 435 mmol) in one portion. After stirring overnight at room temperature, the reaction mixture was concentrated to a thick orange oil. This thick slurry was diluted with 2-propanol (300 mL) and the solid was broken up with a spatula. Filtration afforded a solid which was further rinsed with an additional portion of 2-propanol. Removal of residual 2-propanol was accomplished via high vacuum to afford a light orange solid 7-2. (89.8 g): $^1$H NMR (CDCl$_3$) δ 7.82 (br s, 1H), 7.50 (br s, 1H), 4.41 (t, 1H, 5.3 Hz), 4.24 (q, 2H, 7.1 Hz), 4.09 (d, 2H, 5.9 Hz), 3.47 (dd, 2H, 5.3, 6.2 Hz), 3.40 (s, 6H), 1.30 (t, 3 H, 7.1 Hz).

Ethyl 3-hydroxypyrazin(1H)-2-one-1-acetate (7-3)

A solution of the oxamide (89.8 g, 343 mmol) 2—2, acetic acid (400 mL), and conc. HCl (2 mL) was heated to reflux.

After 1 h the black reaction was concentrated to a thick oil (high vacuum employed to ensure complete removal of AcOH) which was diluted with EtOH (150 mL) and MeOH (150 mL). Scraping the thick black oil with a spatula induced precipitation of the product. The MeOH was removed via rotary evaporation and the remaining slurry was filtered and rinsed with EtOH (200 mL) to deliver a tan solid. Recrystallization from refluxing EtOH (300 mL) afforded an off-white powder 7-3: $^1$H NMR (CD$_3$OD) δ 6.50 (d, 1H, 5.9 Hz), 6.36 (d, 1H, 5.9 Hz), 4.58 (s, 2H), 4.23 (q, 2H, 7.1 Hz), 1.28 (t, 3H, 7.1 Hz). Further crude dione could be obtained upon concentration of the mother liquor.

Ethyl 3-bromopyrazin(1H)-2-one-1-acetate (7-4)

A solution of the hydroxypyrazinone (25.0 g, 126 mmol) 7-3 and phosphorous oxybromide (37.9 g, 132 mmol) in 1,2-dichloroethane (250 mL) was heated to reflux. After 8 h the reaction mixture was treated with sat. aq. Na$_2$CO$_3$ (250 mL) and stirred for 1h. The mixture was diluted with water (100 mL) and dichloromethane (100 mL), the layers were separated and the aqueous layer was backwashed with EtOAc (3×200 mL). The combined organics were dried (MgSO$_4$), and concentrated to give an oil which was stored on a high vacuum line overnite to afford brown solid 7-4: $^1$H NMR (CDCl$_3$) δ 7.17 (d, 1H, 4.2 Hz), 7.07 (d, 1H, 4.2 Hz), 4.65 (s, 2H), 4.27 (q, 2H, 7.2 Hz), 1.31 (t, 3H, 7.2 Hz).

Ethyl 3-(2,2-difluoro-2-(2-pyridylethylamino)pyrazin(1H)-2-one-1-acetate (7-5)

A solution of 4.80 g (30.4 mmol) of 2,2-difluoro-2-(2-pyridyl)ethylamine, 4.24 mL (30.4 mmol) of triethylamine and 7.93 g (30.4 mmol) of ethyl 3-bromopyrazin(1H)-2-one-1-acetate 2-4 was heated to 120° C. in a sealed tube overnight in 12 mL of toluene and 4 mL of ethanol. The reaction was concentrated and the residue was partitioned between dichloromethane and sat. aq. NaHCO$_3$. The aqueous layer was backwashed with 4 portions of dichloromethane. The combined organic layers were dried over MgSO$_4$ and the solvents removed at reduced pressure to give an oil that was chromatographed on SiO$_2$ using 60:40 to 40:60 hexane-EtOAc to give 7-5 as a yellow solid: $^1$H NMR (CDCl$_3$) δ 8.67 (dd, 1H, 4.8, 0.7 Hz), 7.81 (ddd, 1H, 7.8, 7.8, 1.7 Hz), 7.69 (dd, 1H, 7.8, 1 Hz), 7.38 (dd, 1H, 5.1, 7.0 Hz), 6.86 (d, 1H, 4.8 Hz), 6.54 (br t, 1H, 5.9 Hz), 6.40 (d, 1H, 4.6 Hz), 4.54 (s, 2H), 4.38 (td, 2H, 14.0, 6.4 Hz), 4.24 (q, 2H, 7.1 Hz), 1.29 (t, 3H, 7.1 Hz).

Ethyl 3-(2,2-difluoro-2-(2-pyridylethylamino)-6-chloropyrazin(1H)-2-one-1-acetate (7-6)

To a stirred solution of 6.81 g (20.1 mmol) of ethyl 3-(2,2-difluoro-2-(2-pyridylethylamino)pyrazin(1H)-2-one-1-acetate 2-5 and 2.42 g (18.1 mmol) of N-chlorosuccinimide in 100 mL of 1,2-dichloroethane was heated to reflux. An additional 242 mg (1.81 mmol) and 75 mg (0.56 mmol) of NCS were added to the reaction mixture after 1 h and 1.5 h, respectively. After 2.5 h total, the solution was cooled to room temperature and partitioned between dichloromethane (150 mL) and sat. aq. NaHCO$_3$ (200 mL). The layers were separated and the aqueous phase was backwashed with dichloromethane (2×200 mL). The combined organic layers were dried over MgSO$_4$ and the solution concentrated to a volume of 10 mL. This liquid was directly loaded onto a SiO$_2$ column and eluted with 65:35 to 55:45 hexane-EtOAc to give 7-6 as a yellow solid: $^1$H NMR (CDCl$_3$) δ 8.68 (d, 1H, 4.8, Hz), 7.83 (ddd, 1H, 7.7, 7.7, 1.6 Hz), 7.9 (dd, 1H, 7.9 Hz), 7.40 (dd, 1H, 4.9, 7.3 Hz), 6.96 (s, 1H), 6.49 (br t, 1H, 5.9 Hz), 4.89 (s, 2H), 4.38 (td, 2H, 13.9, 6.5 Hz), 4.26 (q, 2H, 7.1 Hz), 1.30 (t, 3H, 7.1 Hz).

3-(2,2-Difluoro-2-(2-pyridylethylamino)-6-chloropyrazin(1H)-2-one-1-acetic acid (7–7)

To a stirred solution of 7.27 g (19.5 mmol) of ethyl 3-(2,2-difluoro-2-(2-pyridylethylamino)-6-chloropyrazin(1H)-2-one-1-acetate 7-6 in 200 mL of methanol was added 39 mL (39.0 mmol) of IM aq. potassium hydroxide. After 3 h the solution was acidified to pH=7 using conc. HCl, and concentrated at reduced pressure (azeotrope with PhCH$_3$) to give a white solid containing potassium chloride and 7-7: $^1$H NMR (CDl$_3$) δ8.64 (d, 1H, 4.8 Hz), 7.93 (ddd, 1H, 7.7, 7.7, 1.5 Hz), 7.70 (d, 1H, 8.0 Hz), 7.49 (dd, 1H, 5.2, 7.4 Hz), 6.80 (s, 1H), 4.67 (s, 2H), 4.27 (t, 2H, 13.9 Hz).

METHOD 8

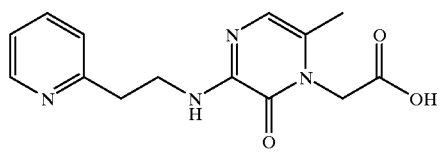

To a solution 9 g (33 mmol) of ethyl 3-bromo-6-methylpyrazin-2-one-1-acetate (see Sanderson et al., WO 99/11267, compound 7-4, pages 34–37 the contents of which are hereby incorporated by reference, referenced above as compound "A") was added 6 mL (50 mmol) 2-(2-pyridyl) ethylamine in 5 mL ethanol and the solution was heated to reflux for 48 hrs. The reaction mixture was diluted with 800 mL EtOAc, washed with 750 mL each of saturated aqueous sodium bicarbonate solution, water, and brine, then dried over Na$_2$SO$_4$, filtered and concentrated. Crystallization from 400 mL of 3:1 hexane:EtOAc gives ethyl 3-(2-(2-pyridyl) ethylamino)-6-methylpyrazin-2-one-1-acetate. Treatment of 2 g(6.3 mmol) of this in 20 mL MeOH with 5 mL (0.66 mmol, 1.32M aqueous solution) LiOH for 3 hours followed by addition of 0.52 L (0.66 mmol, 12N aqueous solution) HCl and filtration afforded 3-(2-(2-pyridyl)ethylamino)-6-methylpyrazin-2-one-1-acetic acid.: $^1$H NMR (CD$_3$OD) δ 8.49 (d, 1H, J=4.3 Hz); 7.83 (dt, 1H, J=7.77 and 1.74 Hz); 7.42 (d, 1H, J=7.86 Hz); 7.33 (m, 111); 6.66 (s, 1H); 4.70 (s, 2H); 3.72 (t, 2H, J=6.95 Hz); 3.12 (t, 2H, J=6.95 Hz); 2.16 (s, 3H).

METHOD 9

Suitable carboxylic acid starting materials for

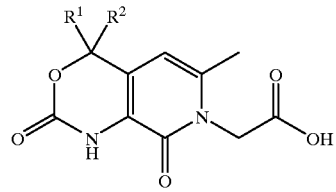

may be prepared according to the following procedures.
General Synthesis

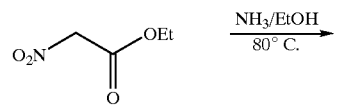

-continued

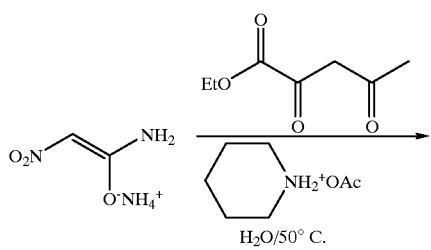

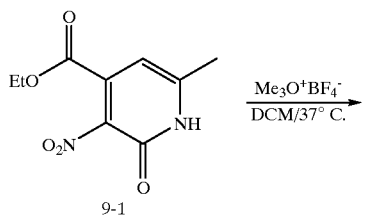

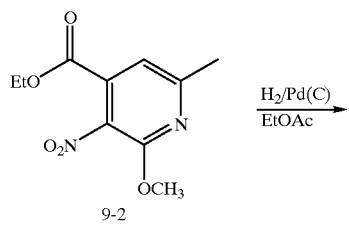

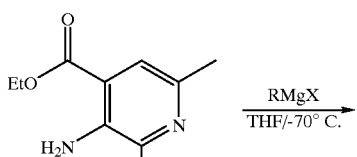

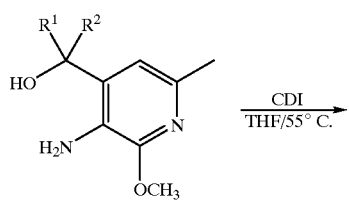

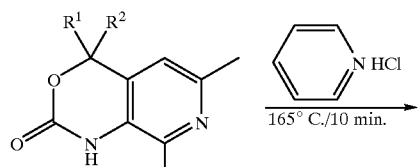

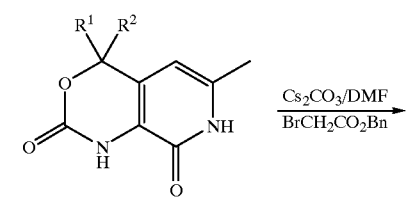

-continued

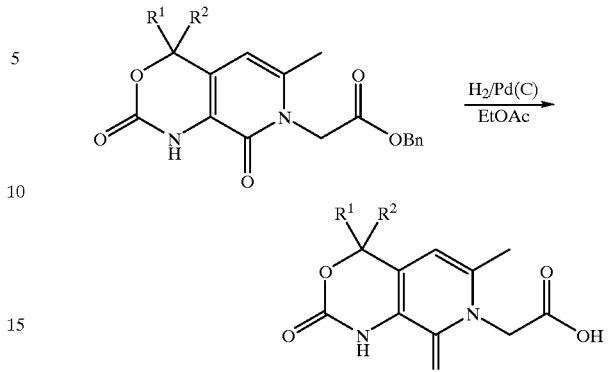

Step A: Ethyl 6-methyl-3-nitropyridone 4-carboxylate (9-1)

9-1

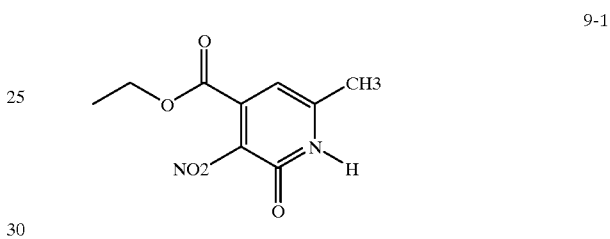

To a slurry nitroacetamide ammonia salt (70.3 g, 581 mmol) in 400 mL of deionized water was added 100 g (633 mmol, 1.09 equiv.) of ethyl 2,4-dioxovalerate followed by a solution of piperdinium acetate (prepared by adding 36 mL of piperdine to 21 mL of acetic acid in 100 mL of water). The resulting solution was stirred at 40° C. for 16 h then cooled in an ice bath. The precipitated product was filtered and washed with 50 mL of cold water to give the above pyridone 9-1 as a yellow solid. $^1$H NMR (CDCl$_3$) δ 6.43 (s, 1H), 4.35 (q, J=7 Hz, 2H), 2.40 (s, 3H), 1.35 (t, J=7 Hz, 3H).

Step B: Ethyl 2-methoxy-6-methyl-3-nitropyridine 4-carboxylate (9-2)

9-2

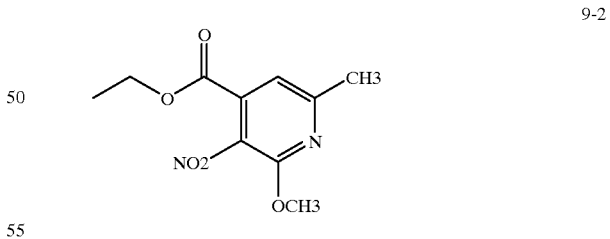

A solution of the pyridone 9-1 from step A (6.2 g, 27.4 mmol) in 50 mL of DCM was treated with 4.47 g (30.2 mmol) of solid trimethyloxonium tetrafluoroborate and the mixture was stirred at 40° C. until the reaction was judged to be complete by HPLC (typically 24–72 h). The reaction mixture was concentrated to one-third volume, loaded onto a silica gel column and eluted with 2:3 EtOAc/Hexane to give the methoxy pyridine 9-2 as a yellow liquid. $^1$H NMR (CDCl$_3$) δ 7.2 (s, 1H), 4.35 (q, J=7 Hz, 2H), 4.05 (s, 3H), 2.55 (s, 3H), 1.35 (t, J=7 Hz, 3H).

Step C: Ethyl 3-amino-2-methoxy-6-methylpyridine 4-carboxylate (9-3)

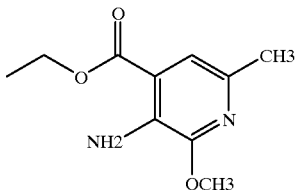

To an oxygen free solution of the nitro ester 1-2 from step B (2.5 g, 10.4 mmol) in 50 mL of EtOAc was added 520 mg of 10% Pd on charcoal. Hydrogen gas was added and the reaction mixture was stirred for 17 h. The solution was filtered through a pad of Celite, concentrated and chromatographed (2:3 EtOAc/Hexane) to give the desired amine 9-3 as a white solid.
$^1$H NMR (CDCl$_3$) δ 7.05 (s, 1H), 5.70 (bs, 2H), 4.35 (q, J=7 Hz, 2H), 3.95 (s, 3H), 2.37 (s, 3H), 1.39 (t, J=7 Hz, 3H).

Step D: Amino alcohol 9-4

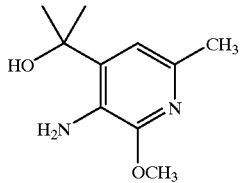

To a −70° C. solution of 260 mg (1.0 mmol) of the ester 1-3 from step C in 5 mL of THF was added 1.2 mL (3.5 mmol) of 3 M MeMgBr. The resulting solution was allowed to warm to ambient temperature over 16 h. The reaction mixture was quenched with 5 mL of saturated NH$_4$Cl solution and the two phases were separated. The aqueous phase was extracted with 10 mL of EtOAc and the combined organic extracts were washed with 5 mL of brine and dried over MgSO$_4$. The yellow solution was concentrated and chromatographed (1:1 EtOAc/Hexane) give alcohol 9-4. $^1$H NMR (CDCl$_3$) δ 6.45 (s, 1H), 4.60 (bs, 1H), 3.95 (s, 3H), 2.55 (s, 3H), 1.60 (s, 6H).

Step E: Oxazinone 9-5

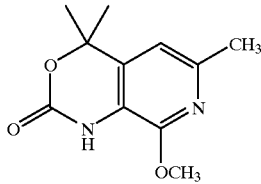

To a solution of 386 mg (2.0 mmol) of the amino alcohol 9-4 from step D in 10 mL of TBF was added 1.62 g (10.0 mmol) of 1,1'-carbonyl diimidazole. The resulting solution was heated at 55° C. over 16 h. The reaction mixture was cooled and the solvent was removed by rotory evaporation. The mixture was redissolved in 50 mL of EtOAc and washed sequentially with 10 mL each of saturated NH$_4$Cl solution, water, then brine. The solution was concentrated and chromatographed (1:1 EtOAc/Hexane) to give oxazinone 9-5. $^1$H NMR (CDCl$_3$) δ 7.17 (bs, 1H), 6.49 (s, 1H), 3.95 (s, 3H), 2.40 (s, 3H), 1.66 (s, 6H).

Step F: Pyridone 9-6

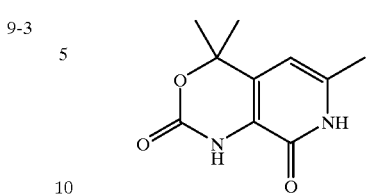

To 333 mg (1.5 mmol) of the oxazinone from step E was added 1.72 g (15.0 mmol) of solid pyridine hydrochloride. The solid mixture was heated at 155° C. for 5 min to effect a melt. The reaction mixture was cooled to rt, quenched with 10 mL of water and stirred for 20 min. The resulting precipitate was filtered and air dried to give pyridone 9-6. $^1$H NMR (DMSO d$_6$) δ 11.85 (bs, 1H), 9.30 (bs, 1H), 6.03 (s, 1H), 2.10 (s, 3H), 1.45 (s, 6H).

Step G: Benzyl Ester 9-7

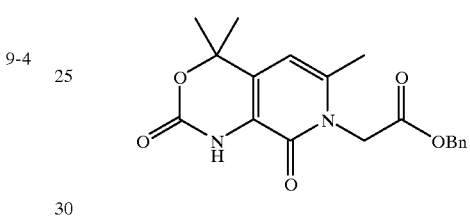

To 186 mg (0.89 mmol) of the pyridone 9-6 from step F in 5 mL of DMF was added 325 mg (1.0 mmol) of Cs$_2$CO$_3$ and 0.158 mL (1.0 mmol) of benzyl 2-bromoacetate. The resulting mixture was stirred at rt for 15 h. The reaction mixture was then evaporated to dryness, redissolved in 20 mL of EtOAc and washed with 3×5 mL of brine. The organic solution was dried over MgSO$_4$ concentrated and chromatographed (EtOAc) to give benzyl ester 9-7. $^1$H NMR (CDCl$_3$) δ 7.45 (bs, 1H), 7.40–7.20 (mn, 5H), 5.90 (s, 1H), 5.25 (s, 2H), 4.82 (s, 2H), 2.30 (s, 3H), 1.65 (s, 6H).

Step H: Carboxylic Acid 9-8

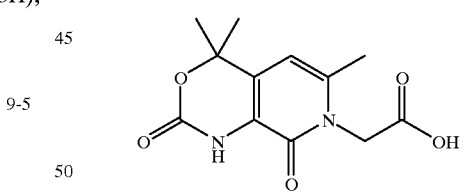

A solution containing 176 mg (0.492 mmol) of the ester 9-7 from step G and 50 mg of 10% Pd on carbon in 12 mL of THF and 6 mL of MeOH was hydrogenated at room temperature under a balloon of H$_2$. After stirring for 20 min, the reaction mixture was filtered through Celite and evaporated to dryness to give acid 9-8. $^1$H NMR (DMSO d$_6$) δ 13.2 (bs, 1H), 9.45 (s, 1H), 6.20 (s, 1H), 4.70 (s, 2H), 2.50 (s, 3H), 1.60 (s, 6H).

Alternative intermediates, where R$^1$ and R$^2$ are other than methyl, may be prepared according to a procedure similar to the one outlined above but reacting 9-3 with an alternative reagent, such as EtMgBr instead of MeMgBr.

Scheme J outlines a procedure for using the intermediate formed according to Scheme I to make a final active compound of the invention.

Scheme J

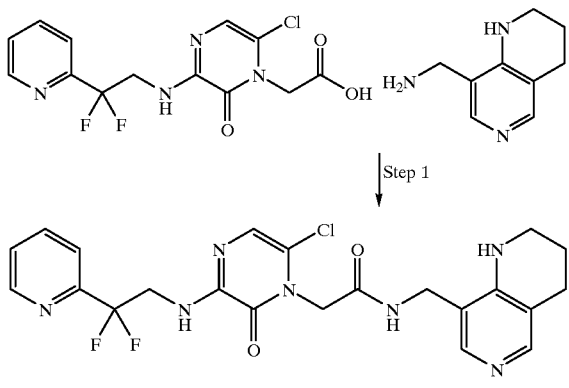

EXAMPLE 1
Procedure for Making an Intermediate According to Scheme A:

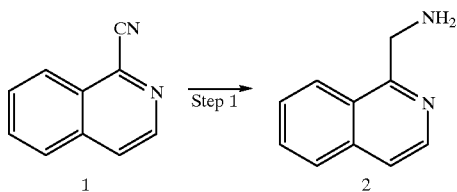

1-(aminomethyl)isoquinoline (2).

To a solution of 0.4999 g (3.24 mmol) 1-isoquinolinecarbonitrile (1) (Aldrich) in 15 mL glacial acetic acid was added 0.0564 g Pd (10% on C). After 16 h under $H_2$ at atmospheric pressure, the reaction mixture was filtered over celite. The celite was washed with 75 mL EtOAc, and the filtrate was concentrated in vacuo. To this was added 100 mL n-heptane, and the mixture concentrated in vacuo. The above step was repeated three times to remove acetic acid. Purification by flash chromatography (40×220 mm silica gel, linear gradient 5–10% (10% $NH_4OH:MeOH$) $:CH_2C_{12}$) yielded 2. $^1H$ NMR ($CDCl_3$, 400 MHz) δ 8.479 (d, 1H, J=5.76 Hz, ArH); 8.135 (d, 1H, J=8.42 Hz, ArH); 7.848 (d, 1H, J=8.41 Hz, ArH); 7.714–7.673 (m, 1H, ArH); 7.639–7.597 (m, 1H, ArH); 7.563 (d, 1H, J=5.67 Hz, ArH); 4.517 (s, 2H, $ArCH_2$); MS (FAB): m/z 159.08 ($M^{30}$ H).

EXAMPLE 2
Procedure for making an intermediate according to Scheme B:

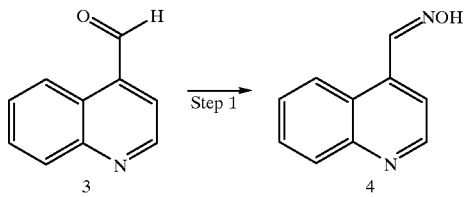

Step 1:4-quinolineoxime 4). To a solution of 1.0089 g (6.42 mmol) 4-quinolinecarboaldehyde (3) in 35 mL absolute ethanol was added 2.1414 g (30.82 mmol) hydroxylamine hydrochloride and 5.099 mL (36.58 mmol) triethylamine. After 18 h at 80° C., the reaction mixture was diluted with 100 mL EtOAc and washed with 50 mL $H_2O$. The aqueous layer was extracted with 25 mL EtOAc, and the combined organic layers were washed with 50 mL brine, dried over $Na_2SO_4$, filtered and concentrated in vacuo. Purification by flash chromatography (40×220 mm silica gel, linear gradient 2–5% $MeOH:CH_2Cl_2$) afforded 4. $^1H$ NMR ($CD_3OD$, 400 MHz) δ 8.845 (d, 1H, J=4.57 Hz, ArH); 8.779 (s, 1H, ArH); 8.627 (d, 1H, J=8.59 Hz, ArH); 8.068 (d, 1H, J=8.50 Hz, ArH); 7.829–7.787 (m, 1H, ArH); 7.764 (d, 1H, J=4.67 Hz, ArH); 7.695–7.653 (m, 1H, ArH); MS (FAB): m/z 173.07 (M+H).

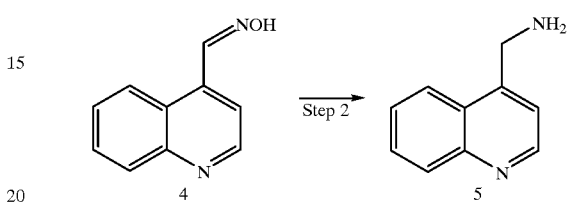

Step 2: 4-(aminomethyl)quinoline (5). To a solution of 0.8571 g (4.98 mmol) 4 in 50 mL 10% AcOH:10% $H_2O$:80% EtOH was added 0.0850 g Pd (10% on C). After 16 h under $H_2$ O at atmospheric pressure, the reaction mixture was filtered over celite. The celite was washed with 250 mL EtOAc, and the filtrate was concentrated in vacuo. To this was added 100 mL n-heptane, and the mixture concentrated in vacuo. The above step was repeated three times to remove acetic acid. Purification by flash chromatography (40×260 mm silica gel, linear gradient 5–20% (10% $NH_4OH:MeOH):CH_2Cl_2$) provided 5. $^1H$ NMR ($CDCl_3$, 400 MHz) δ 8.901 (d, 1H, J 4.39 Hz, ArH); 8.143 (d, 1H, J=8.50 Hz, ArH); 8.025 (d, 1H, J=8.41 Hz, ArH); 7.747–7.706 (m, 1H, ArH); 7.606–7.565 (m, 1H, ArH); 7.480 (d, 1H, J=4.48 Hz, ArH); MS (FAB): m/z 159.09 ($M^+H$).

EXAMPLE 3
Procedure or Making an Intermediate According to Scheme C:

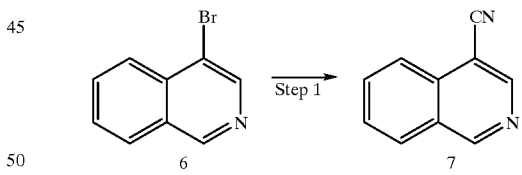

Step 1: 4-isoguinolinecarbonitrile (7).

To a mixture of 3.0442 g (14.63 mmol) 4-bromoisoquinoline (6), 1.0380 g (8.84 mmol) zinc cyanide and 1.0721 g (0.92 mmol) tetrakis(triphenylphosphine) palladium(0) was added 30 mL DMF. After 19 h under argon at 80° C., the reaction mixture was cooled to room temperature, diluted with 150 mL toluene and washed with 80 mL 2N $NH_4OH$ and 40 mL brine. The organic layer was dried over $Na_2SO_4$, filtered and concentrated in vacuo. Purification by flash chromatography (75×110 mm silica gel, 1% $MeOH:CH_2Cl_2$) gave 7. $^1H$ NMR ($CDCl_3$, 400 MHz) 67 9.428 (s, 1H, ArH); 8.915 (s, 1H, ArH); 8.205 (d, 1H, J=8.41 Hz, ArH); 8.113 (d, 1H, J=8.23 Hz, ArH); 7.970–7.929 (m, 1H, ArH); 7.818–7.778 (m, 1H, ArH); MS (Electrospray): m/z 155.0 ($M^+H$).

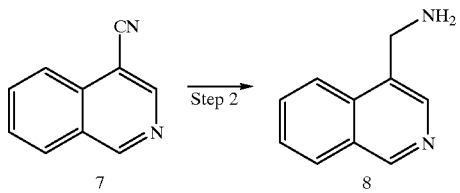

Step 2: 4-(aminomethyl)isoquinoline (8).

To a solution of 0.0934 g (0.61 mmol) 7 in 3 mL $NH_3$ saturated EtOH was added a 1 mL slurry of Raney nickel (50wt. % in EtOH). After 20.5 h under $H_2$ at atmospheric pressure, the reaction mixture was diluted with 50 mL EtOH and filtered over celite. The celite was washed with 200 mL EtOH, and the filtrate was concentrated in vacuo. Purification by flash chromatography (15×140 mm silica gel, 5% (10% $NH_4OH:MeOH):CH_2Cl_2$) produced 8. $^1H$ NMR ($CDCl_3$, 400 MHz) δ 9.190 (s, 1H, ArH); 8.504 (s, 1H, ArH); 8.105 (d, 1H, J=8.50 Hz, ArH); 8.013 (d, 1H, J=8.13 Hz, ArH); 7.793–7.751 (m, 1H, ArH); 7.656–7.616 (m, 1H, ArH); 4.320 (s, 2H, ArCH$_2$); MS (Electrospray): m/z 159.0 ($M^+H$).

EXAMPLE 4

Procedure for Making an Intermediate According to Scheme D:

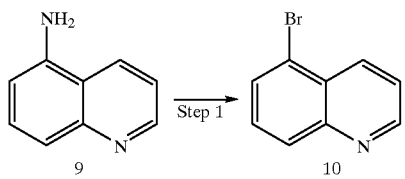

Step 1: 5-bromoquinoline (10).

To a 0° C. mixture of 1.0022 g (6.94 mmol) 5-aminoquinoline (9) and 6 mL 24% aqueous hydrobromic acid was added a solution of 0.5 g (7 mmol) sodium nitrite in 3 mL $H_2O$. After 5 min at 0° C., the mixture was added over 5 min to 1.2026 g (8.38 mmol) cuprous bromide in 10 mL 47% aqueous hydrobromic acid. After stirring at room temperature for 7.5 h, the reaction mixture was basified with ice and 50% aqueous NaOH and filtered. The filtrate was extracted three times with 50 mL ethyl ether, and the combined ether layers were concentrated in vacuo. The resulting residue was combined with precipitate from the above filtration, dissolved in 50% MeOH:$CH_2Cl_2$ and filtered. The filtrate was concentrated in vacuo, dissolved in 10% (10% $NH_4OH:MeOH):CH_2Cl_2$ and filtered over silica. The filtrate was concentrated in vacuo to yield 10. $^1H$ NMR (DMSO, 400 MHz) δ 8.997 (d, 1H, J=2.83 Hz, ArH); 8.525 (d, 1H, J=8.59 Hz, ArH); 8.089 (d, 1H, J=8.50 Hz, ArH); 8.000 (d, 1H, J=7.49 Hz, ArH); 7.741–7.701 Hz (m, 2H, ArH); MS (Electrospray): m/z 207.9, 209.9 ($M^+H$, $^{79}Br$, $^{81}Br$).

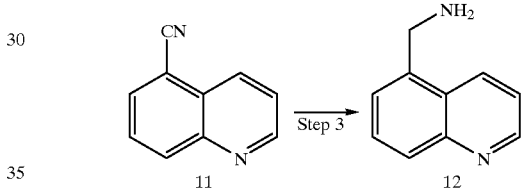

Step 2: 5-quinolinecarbonitrile (11).

To a solution of 0.1810 g (0.870 mmol) 10 in 5 mL DMF was added 0.0630 g (0.54 mmol) zinc cyanide and 0.0640 g (0.055 mmol) tetrakis(triphenylphosphine)palladium(0). After 66 h under argon at 80° C., the reaction mixture was cooled to room temperature, diluted with 40 mL toluene and washed with 10 mL 2N $NH_4H$. The aqueous layer was extracted with 10 mL toluene. The combined organic layers were washed with 10 mL brine, dried over $Na_2SO_4$, filtered and concentrated in vacuo. Purification by flash chromatography (25×130 mm silica gel, linear gradient 2–3% (10% $NH_4OH:MeOH):CH_2Cl_2$) afforded 11. $^1H$ NMR ($CDCl_3$, 400 MHz) 69.065 (dd, 1H, J=1.65, 4.21 Hz, ArH); 8.567 (d, 1H, J=8.50 Hz, ArH); 8.377 (d, 1H, J=8.50 Hz, ArH); 8.005 (dd, 1H, J=1.09, 7.22 Hz, ArH); 7.796 (dd, 1H, J=7.22, 8.59 Hz, ArH); 7.636 (dd, 1H, J=4.21, 8.51 Hz, ArH); MS (Electrospray): m/z 155.0 ($M^+H$).

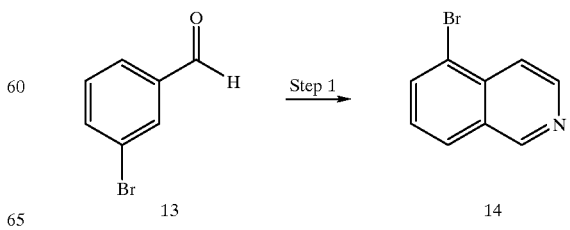

Step 3: 5-(aminomethyl)quinoline (12). To a solution of 0.1173 g (0.76 mmol) 11 in 10 mL $NH_3$ saturated EtOH was added a 1 mL slurry of Raney nickel (50wt. % in EtOH). After 19 h under $H_2$ at atmospheric pressure, the reaction mixture was diluted with 20 mL EtOH and filtered over celite. The celite was washed with 200 mL EtOH, and the filtrate was concentrated in vacuo. Purification by flash chromatography (20×120 mm silica gel, linear gradient 5–7% (10% $NH_4OH:MeOH):CH_2C_2$) provided 12. $^1H$ NMR ($CDCl_3$, 400 MHz) δ 8.937 (dd, 1H, J=1.56, 4.12 Hz, ArH); 8.475 (d, 1H, J=8.14 Hz, ArH); 8.033 (d, 1H, J=8.50 Hz, ArH); 7.681 (t, 1H, J=7.78 Hz, ArH); 7.546 (d, 1H, J=7.04 Hz, ArH); 7.450 (dd, 1H, J=4.16, 8.55 Hz, ArH); 4.347 (s, 2H, ArCH$_2$); MS (Electrospray): m/z 159.0 ($M^+H$).

EXAMPLE 5

Procedure for Making an Intermediate According to Scheme E:

Scheme E

Step 1: 5-bromoisoquinoline (14)

A mixture of 3.5 mL (30 mmol) 3-bromobenzaldehyde (13) and 5 mL (34 mmol) aminoacetaldehyde diethyl acetal was heated to 100° C. for 2.5 h, then cooled to room temperature to give a two-phase mixture. The product oil was carefully separated from the water droplets and distilled under high vacuum (bp 128° C. @ <1 mmHg) to give 8.8 g of an oil that was added slowly to 50 g of concentrated $H_2SO_4$, and the resulting mixture added to a 160° C. solution of 10 g $P_2O_5$ in 5 mL $H_2SO_4$. This mixture was stirred manually with a glass rod for 15 min, cooled for 5 min, then poured into 1 L of ice. This was transferred to a separatory funnel and washed with 200 mL ether, brought to pH 10 with concentrated NaOH (adding ice to keep it cool), and extracted 3×200 mL EtOAc. The combined EtOAc extracts were washed with brine, dried over $Na_2SO_4$, filtered and concentrated to give 2 g of a 1:1 mixture of 5 and 7-bromoisoquinoline that was used without further purification.

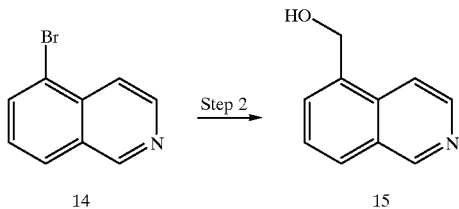

14　　　　　　　　　　　15

Step 2: 5-(hydroxymethyl)isoquinoline (15)

To a solution of 2 g (9.6 mmol) of the 1:1 mixture of 5 and 7-bromoisoquinoline in 7 mL DMSO and 15 mL MeOH was added 0.4 g (1 mmol) 1,3-bis(diphenylphosphino)propane, 0.2 g (0.9 mmol) Pd(OAc)2, and 5 mL (36 mmol) $Et_3N$. Carbon monoxide gas was bubbled through the solution for 5 minutes, and then the reaction was heated under a CO atmosphere for 36 h. The reaction mixture was cooled, diluted with 300 mL EtOAc, washed with 200 mL saturated sodium bicarbonate solution and 200 mL brine, then dried over $Na_2SO_4$, filtered and concentrated. Purification by silica gel chromatography (4×12 cm silica gel, linear gradient 1–4% MeOH containing 10% saturated aqueous $NH_4OH/CH_2Cl_2$ afforded 1.3 g of 5- and 7-carboxymethyl isoquinoline as an inseparable mixture.

To a −78° C. solution of 1.2g (6.4 mmol) 5- and 7-carboxymethyl isoquinoline in 50 mL $CH_2Cl_2$ was added 15 mL (15 mmol, IM solution in $CH_2Cl_2$) diisobutulaluminum hydride. After 30 min at −78° C. the reaction was quenched with 10 mL IM HCl, allowed to warm to room temperature, diluted with 250 mL EtOAc, and brought to pH>10 with 250 mL saturated sodium bicarbonate solution. The layers were mixed and separated and the EtOAc layer was washed with 250 mL brine, then dried over $Na_2SO_4$, filtered and concentrated. Purification by silica gel chromatography (4×12 cm silica gel, linear gradient 3–10% MeOH containing 10% $NH_4OH/CH_2Cl_2$ followed by purification of mixed fractions (3×12 cm silica gel, linear gradient 3–10% MeOH containing 10% $NH_4OH/CH_2Cl_2$) afforded 5-hydroxymethylisoquinoline 15 as the higher Rf isomer: $^1$H NMR(400 mHz, $CDCl_3$) 9.25 (s, 1H); 8.57 (d, IH, J=5.94 Hz); 7.92 (d, 1H, J=8.23 Hz); 7.90 (d, 1H, J=6.04 Hz); 7.76 (d, 1H, J=6.22Hz); 7.59 (dd, 1H, J=7.13 and 8.05 Hz); 5.16 (s, 2H). The lower Rf isomer is the 7-isomer. $^1$H NMR(400 mHz, $CDCl_3$) 9.22 (s, 1H); 8.51 (d, 1H, J=5.76 Hz); 7.95 (br s, 1H); 7.83 (d, 1H, J=8.41 Hz); 7.71 (dd, 1H, J=8.5 and 1.65 Hz); 7.65 (d, 1H, J=5.76 Hz); 4.92 (s, 2H).

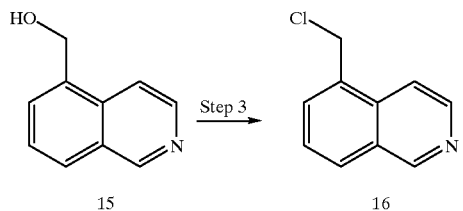

15　　　　　　　　　　　16

Step 3: 5-(chloromethyl)isoquinoline (16).

To a solution of 0.1212 g (0.76 mmol) 15 in 8 mL $CH_2Cl_2$ at 0° C. was added 64.8 μL (0.84 mmol) methanesulfonyl chloride and 84.7 μL (0.61 mmol) triethylamine. After 3 h at 0° C., the reaction mixture was warmed to room temperature and 32.0 μL (0.23 mmol) triethylamine added. The reaction was recooled to 0° C., and 14.7 μL (0.19 mmol) methanesulfonyl chloride and 26.5 μL (0.19 mmol) triethylamine were added. After 62 h at room temperature, the reaction mixture was diluted with 25 mL $CH_2Cl_2$ and washed with 10 mL saturated $NaHCO_3$ solution. The aqueous layer was extracted with 10 mL $CH_2Cl_2$, and the combined organic layers were washed with 10 mL brine, dried over $Na_2SO_4$, filtered and concentrated in vacuo. The product was purified by flash chromatography (15×140 mm silica gel, 2% (10% $NH_{40}H$:MeOH):$CH_2Cl_2$). Mixed fraction repurified by flash chromatography (12×75 mm silica gel, 1% (10% $NH_{40}H$:MeOH):$CH_2Cl_2$) to give 16. $^1$H NMR ($CDCl_3$, 400 MHz) δ 9.305 (s, 1H, ArH); 8.653 (d, 1H, J=5.85 Hz, ArH); 7.992 (d, 1H, J=8.23 Hz, ArH); 7.927 (d, 1H, J=5.94 Hz, ArH); 7.753 (d, 1H, J=7.04 Hz, ArH); 7.583 (dd, 1H, J=7.14, 8.14 Hz, ArH); 5.020 (s, 1H, ArCH$_2$); MS (Electrospray): m/z 177.9, 179.9 (M$^+$H, $^{35}$Cl, $^{37}$Cl).

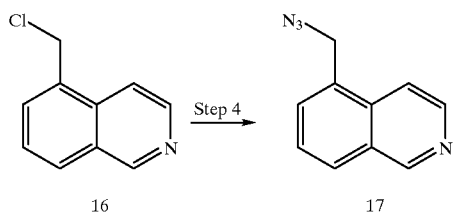

16　　　　　　　　　　　17

Step 4: 5-(azidomethyl)isoquinoline (17).

To a solution of 0.0415 g (0.23 mmol) 16 in 3 mL DMF was added 0.0169 g (0.26 mmol) sodium azide. After a 3 h, an additional 0.0033g (0.05 mmol) portion of sodium azide was added. After 24 h at room temperature, the reaction mixture was diluted with 50 mL EtOAc and washed with 20 mL brine. The aqueous layer was extracted with 10 mL EtOAc. The combined organic layers were dried over $Na_2SO_4$, filtered and concentrated in vacuo. Purification by flash chromatography (10×175 mm silica gel, linear gradient 5–20% EtOAc:hexane) produced 17. $^1$H NMR ($CDCl_3$, 400 MHz) δ 9.318 (s, 1H, ArH); 8.637 (d, 1H, J=6.10 Hz, ArH); 8.010 (d, 1H, J=7.94 Hz, ArH); 7.822 (d, 1H, J=6.10 Hz, ArH); 7.713 (d, 1H, J=7.02 Hz, ArH); 7.617 (dd, 1H, J=7.17, 8.09 Hz, ArH); 4.774 (s, 1H, ArH); MS (Electrospray): m/z 185.0 (M$^+$H).

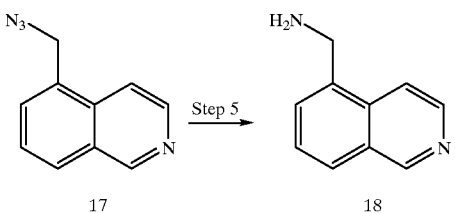

Step 5: 5-(aminomethyl)isoquinoline (18).

To a solution of 0.0282 g (0.15 mmol) 17 in 1 mL EtOAc was added 0.0034 g Pd (10% on C). After 5 h under $H_2$ at atmospheric pressure, the reaction mixture was diluted with 30 mL EtOAc and filtered over celite. The celite was washed with 200 mL EtOAc, and the filtrate was concentrated in vacuo. Purification by flash chromatography (10×160 mm silica gel, 5% (10% $NH_4OH$:MeOH):$CH_2Cl_2$) yielded 18. $^1$H NMR (CDCl$_3$, 400 MHz) δ 9.272 (s, 1H, ArH); 8.583 (d, 1H, J=5.94 Hz, ArH); 7.876 (dd, 2H, J=7.18, 11.57 Hz, ArH); 7.583 (t, 1H, J=7.64 Hz, ArH); MS (Electrospray): m/z 159.0 (M$^+$H).

EXAMPLE 6
Procedure for Making an Intermediate According to Scheme F:

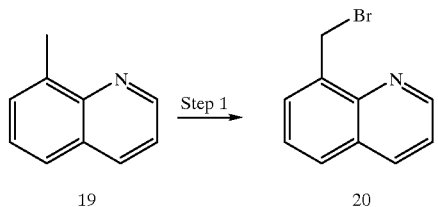

8-(bromomethyl)quinoline (20).

To a solution of 1.1890 g (8.30 mmol) 8-methylquinoline (19) in 35 mL CCl$_4$ was added 1.5512 g (8.72 mmol) N-bromosuccinimide and 0.0824 g (0.50 mmol) 2,2'-azobisisobutyronitrile. After 23 h at 80° C., the reaction mixture was diluted with 70 mL CCl$_4$. The succinimide solid was removed by vacuum filtration and washed with 100 mL CCl$_4$. The filtrate was concentrated in vacuo. Purification by flash chromatography (60×190 mm silica gel, linear gradient 20–40% (EtOAc:hexane) afforded 20. 1H NMR (CDCl$_3$, 400 MHz) δ 9.018 (dd, 1H, J=1.74,4.21 Hz, ArH); 8.173 (dd, 1H, J=1.79, 8.28 Hz, ArH); 7.855–7.796 (m, 2H, ArH); 7.521 (dd, 1H, J=7.13, 8.23 Hz, ArH); 7.455 (dd, 1H, J=4.17, 8.28 Hz, ArH); 5.251 (s, 2H, ArCH$_2$); MS (Electrospray): m/z 221.99, 223.99 (M$^+$H, $^{79}$Br, $^{81}$Br).

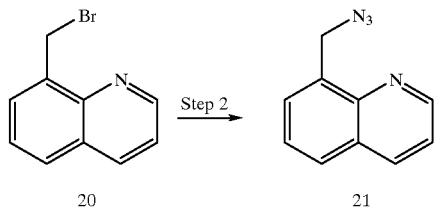

Step 2: 8-(azidomethyl)quinoline (21).

To a solution of 1.0119 g (4.56 mmol) 20 in 25 mL of DMF was added 0.3557 g (5.47 mmol) sodium azide. After 4.5 h at room temperature, the reaction mixture was diluted with 80 mL EtOAc and washed with 40 mL brine. The aqueous layer was extracted with 20 mL EtOAc. The combined organics were dried over Na$_2$SO$_4$, filtered and concentrated in vacuo. Purification by flash chromatography (60×220 mm silica gel, linear gradient 5–20% (EtOAc:hexane) provided 21. $^1$H NMR (CDCl$_3$, 400 MHz) δ 8.965 (dd, 1H, J=1.74, 4.21 Hz, ArH); 8.185 (dd, 1H, J=1.74, 8.32 Hz, ArH); 7.823 (dd, 1H, J=1.12, 8.32 Hz, ArH); 7.743 (d, 1H, J=6.95 Hz, ArH); 7.555 (dd, 1H, J=7.18, 8.10 Hz, ArH); 7.455 (dd, 1H, J=4.21, 8.23 Hz, ArH); 5.065 (s, 2H, ArCH$_2$).

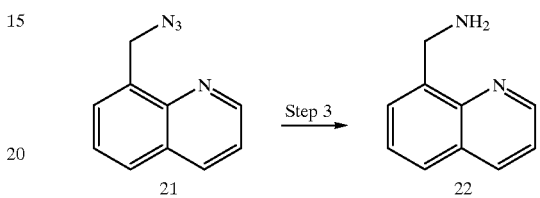

Step 3: 8-(aminomethyl)quinoline (22).

To a solution of 0.8432 g (4.58 mmol) 21 in 20 mL EtOAc was added 0.0880 g Pd (10% on C). After 19 h under H$_2$ at atmospheric pressure, the reaction mixture was diluted with 25 mL EtOAc and filtered over celite. The celite was washed with 150 mL EtOAc, and the combined organics were dried over Na$_2$SO$_4$, filtered and concentrated in vacuo. Purification by flash chromatography (40×140 mm silica gel, linear gradient 5–15% (10% NH$_4$OH:MeOH):CH$_2$Cl$_2$) gave 22. $^1$H NMR (CDCl$_3$, 400 MHz) δ 8.936 (dd, 1H, J=1.78, 4.16 Hz, ArH); 8.165 (dd, 1H, J=1.69, 8.28 Hz, ArH); 7.730 (dd, 1H, J=1.10, 8.14 Hz, ArH); 7.652 (dd, 1H, J=0.64, 7.03 Hz, ArH); 7.497 (t, 1H, J=7.59 Hz, ArH); 7.421 (dd, 1H, J=4.22, 8.23 Hz, ArH); 4.433 (s, 2H, ArCH$_2$); MS (FAB): m/z 159.09 (M$^+$H).

EXAMPLE 7
Procedure for Making an Intermediate According to Scheme G:

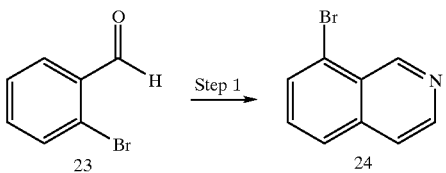

8-bromoisoquinoline (24).

To 7.0 mL (60.0 mmol) 2-bromobenzaldehyde (23) was added 10.0 mL (69.0 mmol) aminoacetaldehyde diethyl acetal. After 3 h at 100° C., the reaction mixture was cooled to room temperature and the layers separated. The organic layer was purified by vaccum distillation to give 15.89 g bromobenzalaminoacetal (b.p. 141–148° C. at approximately 1 mm Hg). To 143 g concentrated sulfuric acid at 0° C. was added 15.89 g bromobenzalaminoacetal. With mechanical stirring, the resulting mixture was added in portions over 5 min to 20 g phosphoric anhydride in 10 g concentrated sulfuric acid maintained at 160° C. After 25 min at 160° C., the reaction mixture was cooled, poured onto ice and washed with 300 mL ethyl ether. The aqueous layer was basified with solid NaOH to pH=10 and extracted with EtOAc repeatedly. The combined EtOAc layers were washed with brine, dried over Na$_2$SO$_4$, filtered and concentrated in vacuo. Purification by flash chromatography (75× 110 mm silica gel, linear gradient 0.5–3% (10% NH$_4$H:MeOH):CH$_2$Cl$_2$) produced 24. $^1$H NMR (CDCl$_3$, 400 MHz) 89.627 (s, 1H, ArH); 8.622 (d, 1H, J=5.67 Hz, ArH); 7.858 (dd, 1H, J=0.87, 7.45 Hz, ArH); 7.799 (d, 1H, J=8.32 Hz, ArH); 7.631 (d, 1H, J=5.76 Hz, ArH); 7.538 (dd, 1H, J=7.50, 8.23 Hz, ArH); MS (Electrospray): m/z 207.9, 209.0 (M$^+$H, $^{79}$Br, $^{81}$Br).

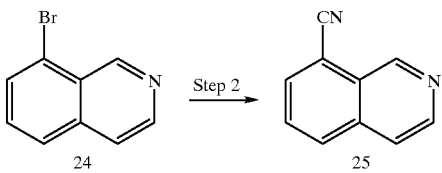

Step 2: 8-isoquinolinecarbonitrile (25).

To a solution of 0.5035 g (2.42 mmol) 24 in 10 mL DMF was added 0.1713 g (1.45 mmol) zinc cyanide and 0.1687 g (0.15 mmol) tetrakis(triphenylphosphine)palladium(0). After 70.5 h under argon at 80° C., the reaction mixture was cooled to room temperature, diluted with 50 mL toluene and washed with 15 mL 2N NH$_4$H. The aqueous layer was extracted with 15 mL toluene. The combined organic layers were washed with 15 mL brine, dried over Na$_2$SO$_4$, filtered and concentrated in vacuo. Purification by flash chromatography (40×105 mm silica gel, linear gradient 1–4% MeOH:CH$_2$Cl$_2$) yielded 25. $^1$H NM (CDCl$_3$, 400 MHz) δ 9.679 (s, 1H, ArH); 8.732 (d, 1H, J=5.67 Hz, ArH); 8.097 (d, 1H, J=8.41 Hz, ArH); 8.031 (d, 1H, J=7.13, ArH); 7.771 (dd, 2H, J=6.81, 10.47 Hz, ArH); MS (Electrospray): m/z 155.0 (M$^+$H).

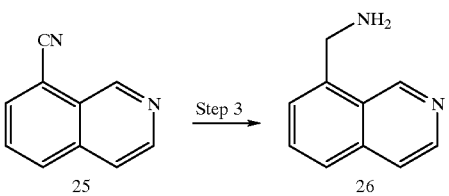

Step 3: 8-(aminomethyl)isoquinoline (26).

To a solution of 0.1787 g (1.16 mmol) 25 in 10 mL NH$_3$ saturated EtOH was added a 1 mL slurry of Raney nickel (50 wt. % in EtOH). After 22 h under H$_2$ at atmospheric pressure, the reaction mixture was diluted with 25 mL EtOH and filtered over celite. The celite was washed with 200 mL EtOH, and the filtrate was concentrated in vacuo. Purification by flash chromatography (15×140 mm silica gel, linear gradient 5–8% (10% NH$_4$HO:MeOH):CH$_2$Cl$_2$) afforded 26. $^1$H NMR (CDCl$_3$, 400 MHz) δ 9.565 (s, 1H, ArH); 8.565 (d, 1H, J=5.66 Hz; ArH); 7.734 (d, 1H, J=8.13 Hz, ArH); 7.679–7.662 (m, 1H, ArH); 7.644 (d, 1H, J=8.14 Hz, ArH); 7.599 (d, 1H, J6.95 Hz, ArH); 4.460 (s, 2H, ArCH$_2$); MS (Electrospray): m/z 159.0 (M$^+$H).

EXAMPLE 8

Procedure for Making an Intermediate According to Scheme H:

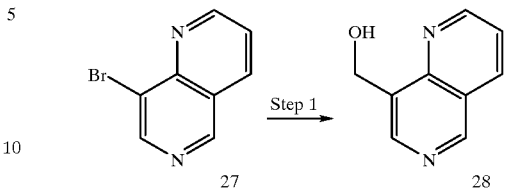

8-hydroxymethyl-1,6-napthyridine (28):

Through a solution of 3 g (14 mmol) 8-bromo-1,6-napthyridine[4] in 700 mL DMF was passed a steady stream of CO gas for 1 h. To this was added 1.8 g (26 mmol) sodium fonnate and 1.5 g (2.1 mmol) (Ph$_3$P)$_2$PdCl$_2$. The resulting mixture was heated to 95° C. while continuing to bubble CO gas through the mixture for 4 h., then concentrated in vacuo. The residue was treated with 100 mL CH$_2$Cl$_2$ and filtered through celite (2×100 mL CH$_2$Cl$_2$ wash). The resulting filtrates were combined and concentrated to give 3.8 g orange oil that was taken up in 100 mL dry CH$_2$Cl$_2$ and cooled to –78 ° C. whereupon 14 mL (14 mmol, IM solution in CH$_2$Cl$_2$) diisobutylalumnium hydride was quickly added by syringe. The resulting mixture was stirred at –78° C. for 30 min., then poured into a well stirred mixture of 600 mL saturated aqueous sodium/potassium tartrate and 600 mL EtOAc, stirred at room temperature for 6 hours, then filtered through Celite. The layers were then separated and the aqueous layer extracted 3×400 mL EtOAc. The combined EtOAc extracts were dried over Na$_2$SO$_4$, filtered and concentrated in vacuo. Purification by flash chromatography (50×120 mm silica gel, linear gradient 3–8% MeOH:CH$_2$Cl$_2$) yielded 8-hydroxymethyl-1,6-napthyridine 28. $^1$H NMR (CDCl$_3$, 400 MHz) δ 9.25 (s, 1H); 9.09 (dd, 1H, J=4.3 and 1.74 Hz); 8.68 (s, 1H); 8.35 (dd, 1H, J=8.3 and 1.74 Hz); 7.60 (dd, 1H, J=8.3 and 4.3 Hz); 5.22 (d, 2H, J=6.59Hz); 4.42 (t, 1OH, J=6.58 Hz). Electrospray mass spectrum M+H=160.9.

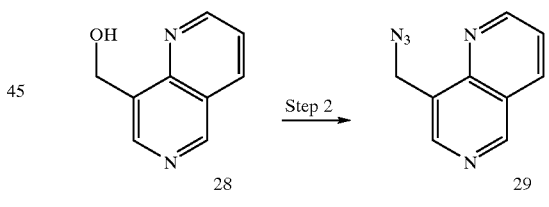

Step 2: 8-azidomethyl-1,6-napthyridine (29):

To a solution of 0.93 g (5.8 mmol) 8-hydroxymethyl-1, 6-napthyridine in 20 mL TBF was added 1.5 mL (7 mmol) DPPA and 1.2 mL (6.7 mmol) DBU. The reaction mixture was allowed to stir at room temperature 18 hours, then another 0.3 mL DPPA and 0.25 mL DBU were added and the reaction mixture heated to 50° C. for 8 hours then cooled to room temperature then another 0.3 mL DPPA and 0.25 mL DBU were added and the reaction mixture was allowed to stir 18 more hours at room temperature. The resulting solution was then diluted with 200 L EtOAc, washed with saturated NaHCO$_3$ solution, and brine, dried over Na$_2$SO$_4$, filtered and concentrated in vacuo. Purification by flash chromatography (40×120 mm silica gel, linear gradient 2–15% MeOH:CH$_2$Cl$_2$) yielded 8-hydroxymethyl-1,6-napthyridine and 8-azidomethyl-1,6-napthyridine. $^1$H NMR (CDCl$_3$, 400 MHz) δ 9.30 (s, 1H); 9.16 (dd, 1H, J=4.3 and 1.8 Hz); 8.78 (s, 1H); 8.35 (dd, 1H, J=8.3 and 1.74 Hz); 7.61 (dd, 1H, J=8.3 and 4.3 Hz); 5.00 (s, 2H).

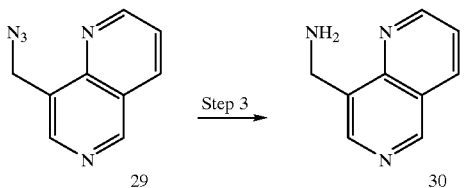

Step 3: 8-aminomethyl-1,6-napthyridine (30):
To a solution of 1.1 g (5.9 mmol) 8-azidomethyl-1,6-napthyridine in 20 mL THF was added 2 mL H₂O and 3 g PPh₃. The resulting solution was alloed to stir overnight at room temperature, then concentrated in vacuo. Purification by flash chromatography (50×140 mm silica gel, linear gradient 5–20% (10% NH₄H in MeOH):CH₂Cl₂) yielded 8-aminomethyl-1,6-napthyridine. ¹H NMR (CDCl₃, 400 MHz) δ 9.22 (s, 1H); 9.13 (dd, 1H, J=4.3 and 1.8 Hz); 8.70 (s, 1H); 8.32 (dd, 1H, J=8.24 and 1.83 Hz); 7.61 (dd, 1H, J=8.24 and 4.3 Hz); 4.40 (s, 2H).

EXAMPLE 9
Procedure for Making an Intermediate According to Scheme I:

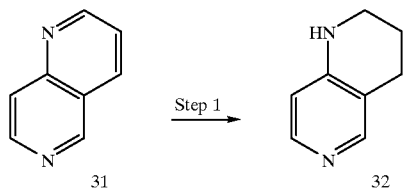

Step 1: 1,2,3,4-tetrahydronapthyridine (32).
To a solution of 0.8315 g (6.39 mmol) 1,6-naphthyridine in 25 mL EtOH was added 0.0875 g Pd (10% on C). The reaction mixture was stirred under H₂ at atmospheric pressure. After 24 h, an additional 0.0431 g Pd (10% on C) was added. After a total of 46 h under H₂ at atmospheric pressure, the reaction mixture was diluted with 50 mL EtOH and filtered over celite. The celite was washed with 300 mL EtOH, and the filtrate concentrated in vacuo. Purification by flash chromatography (50×105 mm silica gel, linear gradient 5–10% (10% NH₄H:MeOH):CH₂Cl₂) yielded 32. ¹H NMR (CDCl₃, 400 MHz) δ 7.969 (d, 2H, J=4.94 Hz, ArH); 6.279 (d, 1H, J=5.57 Hz, ArH); 3.361–3.326 (m, 2H, CH₂); 2.703 (t, 2H, J=6.27 Hz, CH₂); 1.962–1.903 (m, 2H, CH₂); MS (Electrospray): m/z 134.9 (M⁺H).

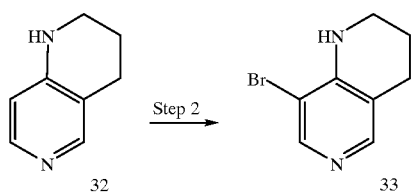

Step 2: 8-bromo-1,2,3,4-tetrahydronapthyridine (33).
To a solution of 0.6730 g (5.02 mmol) 32 in 20 mL glacial acetic acid was added 1.0701 g (6.01 mmol) N-bromosuccinimide. After 16 h at 65° C., the reaction mixture was cooled to room temperature and poured onto 50 mL ice water. This was brought to pH 11 with K₂CO₃ and extracted with 4×100 mL CHCl₃. The combined CHCl₃ extracts were washed with 100 mL brine, dried over Na₂SO₄, filtered and concentrated in vacuo. Purification by flash chromatography (50×115 mm silica gel, linear gradient 2–5% (10% NH₄H:MeOH):CH₂Cl₂) yielded 33. ¹H NMR (CDCl₃, 400 MHz) δ 8.175 (s, 1H, ArH); 7.877 (s, 1H, ArH); 3.458–3.423 (m, 2H, CH₂); 2.725 (t, 2H, J=6.26 Hz, CH₂); 1.970–1.911 (m, 2H, CH₂); MS (Electrospray): m/z 212.9, 214.8 (M⁺H, ⁷⁹Br, ⁸¹Br).

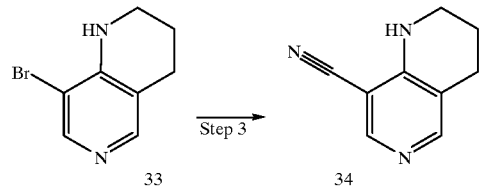

Step 3: 8-cyano-1,2,3,4-tetrahydronapthyridine (34).
To a solution of 0.8914 g (4.18 mmol) 33 in 20 mL DMF was added 0.2949 g (2.51 mmol) zinc cyanide and 0.4825 g (0.42 mmol) tetrakis(triphenylphosphine)palladium(0). After 17 h at 100° C., the reaction mixture was cooled to room temperature, diluted with 120 mL toluene and washed 60 mL 2N NH₄₀H. The aqueous layer was extracted with 60 mL toluene. The combined organic layers were washed with 60 mL brine, dried over Na₂SO₄, filtered and concentrated in vacuo. Purification by flash chromatography (50×80 mm silica gel, 5% (10% NH₄OH:MeOH):CH₂Cl₂) yielded 0.7609 g of 34 and triphenylphosphine oxide. This material was partitioned between 50 mL ethyl ether and 50 mL 1M HCl. The aqueous layer was brought to pH 12 with 50% aqueous NaOH and extracted with 3×100 mL CH₂Cl₂. The combined CH₂Cl₂ layers were washed with 100 mL brine, dried over Na₂SO₄, filtered and concentrated in vacuo to give 34. ¹H NMR (CDCl₃, 400 MHz) δ 8.276 (s, 1H, ArH); 8.037 (s, 1H, ArH); 3.487–3.452 (m, 2H, CH₂); 2.729 (t, 2H, J=6.22 Hz, CH₂); 2.001–1.942 (m, 2H, CH₂); MS (Electrospray): n/z 159.9 (M⁺H).

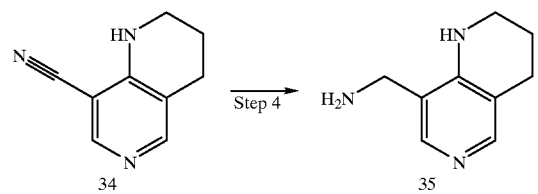

Step 4: 8-aminomethyl-1,2,3,4-tetrahydronapthyridine-(35).
To a solution of 0.5109 g (3.21 mmol) 34 in 15 mL NH₃ saturated EtOH was added a 1 mL slurry of Raney nickel (50 wt. % in EtOH). The reaction mixture was stirred under H₂ at atmospheric pressure. After 23 h, an additional 1 mL slurry of Raney nickel was added. After 44 h, another 1 mL slurry of Raney nickel was added. After a total of 67 h under H₂ at atmospheric pressure, the reaction mixture was diluted with 50 mL EtOH and filtered over celite. The celite was washed with 300 mL EtOH, and the filtrate was concentrated in vacua. Purification by flash chromatography (40×70 mm silica gel, linear gradient 5–10% (10% NH₄H:MeOH):CH₂Cl₂) yielded 35. ¹H NMR (CDCl₃, 400 MHz) δ 7.912 (s, 1H, ArH); 7.846 (s, 1H, ArH); 3.841 (s, 2H, ArCH₂); 3.388 (s, 2H, CH₂); 2.721 (t, 2H, J=6.18 Hz, CH₂); 1.955–1.896 (m, 2H, CH₂); MS (Electrospray): m/z 163.9 (M⁺H).

EXAMPLE 10

Procedure for Making a Compound of the Invention According to Scheme J:

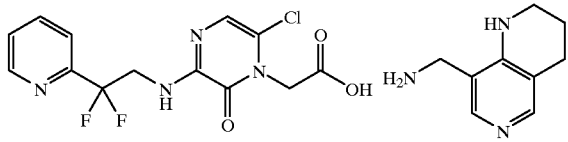

↓

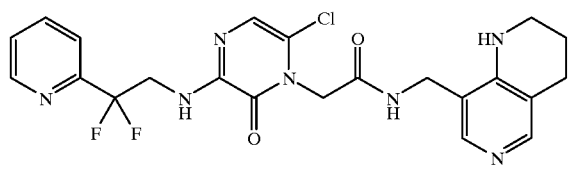

To a solution of 0.0290 g (0. 18 mmol) 8-aminomethyl-1,2,3,4-tetrahydronapthyridine in 2 mL DMF was added 0.0650 g (0.17 mmol) 2-[3-(2,2-diflouro-2-(2-pyridyl)ethylamino)-6-chloropyrazin-2-one-1-yl]-acetic acid, 0.0279 g (0.21 mmol) HOAt and 0.0426 g (0.22 mmol) EDC. After 16 h at room temperature, the reaction mixture was diluted with 30 mL EtOAc and washed with 30 mL saturated NaHCO$_3$ solution. The aqueous layer was extracted with 30 mL EtOAc. The combined organics layers were washed with 30 mL brine, dried over Na$_2$SO$_4$, filtered and concentrated in vacuo. Purification by flash chromatography (15×150 mm silica gel, linear gradient 10% (10% NH$_4$OH:MeOH):CH$_2$Cl$_2$) yielded 2-[3-(2,2-difluoro-2-(2-pyridyl)ethylamino)-6-chloropyrazin-2-one-1-yl]-N-(8-(1,2,3,4,-tetrahydronapthyridinylmethyl) acetamide. $^1$H NMR (CD$_3$OD, 400 MHz) δ 8.636 (d, 1H, J=4.48 Hz, ArH); 7.958–7.919 (m, 1H, ArH); 7.787 (s, 1H, ArH); 7.745 (s, 1H, ArH); 7.707 (d, 1H, J=7.87 Hz, ArH); 7.521–7.489 (m, 1H, ArH); 6.850 (s, 1H, ArH); 4.322–4.248 (m, 4H, CH$_2$); 3.344 (t, 2H, J=5.72 Hz, CH$_2$); 2.706 (t, 2H, J=6.22 Hz, CH$_2$); 1.887–1.842 (m, 2H, CH$_2$); MS (Electrospray): m/z 490.2 (M$^+$H).

Using a coupling procedure similar to the one outlined above, the following compounds were prepared,

EXAMPLE 11

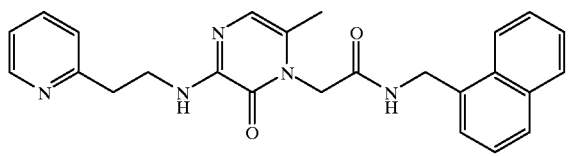

2-[3-(2-(2-pyridyl)ethylamino)-6-methylpyrazin-2-one-1-yl]-N-(1-napthylmethyl)-acetamide High resolution mass spectrum M$^+$H=428.2103

EXAMPLE 12

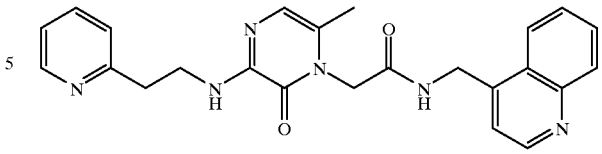

2-[3-(2-(2-pyridyl)ethylamino)-6-methylpyrazin-2-one-1-yl]-N-(4-quinolinylylmethyl)-acetamide
Electrospray mass spectrum M$^+$H=429.2

EXAMPLE 13

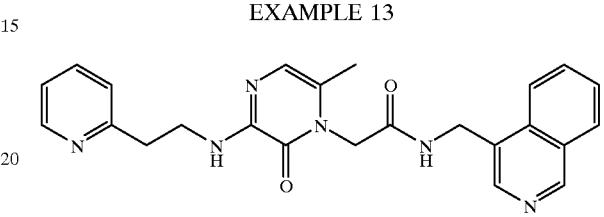

2-[3-(2-(2-pyridyl)ethylamino)-6-methylpyrazin-2-one-1-yl]-N-(4-isoquinolinylylmethyl)-acetamide
Electrospray mass spectrum M$^+$H=429.3

EXAMPLE 14

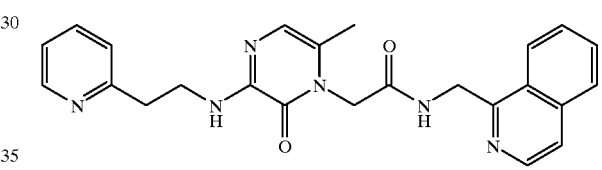

2-[3-(2-(2-pyridyl)ethylamino)-6-methylpyrazin-2-one-1-yl]-N-(1-isoquinolinylylmethyl)-acetamide
Electrospray mass spectrum M$^+$H=429.2

EXAMPLE 15

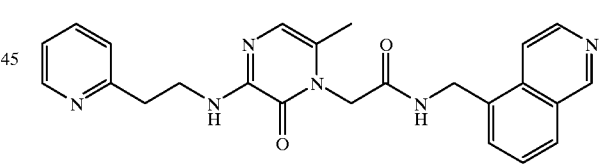

2-[3-(2-(2-pyridyl)ethylamino)-6-methylpyrazin-2-one-1-yl]-N-(5-isoquinolinylylmethyl)-acetamide
High resolution mass spectrum M$^+$H=429.3

EXAMPLE 16

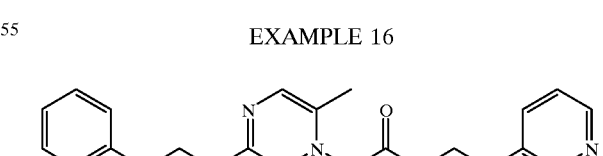

2-[3-(2-(2-pyridyl)ethylamino)-6-methylpyrazin-2-one-1-yl]-N-(5-quinolinylylmethyl)-acetamide
High resolution mass spectrum M$^+$H=429.2037

EXAMPLE 17

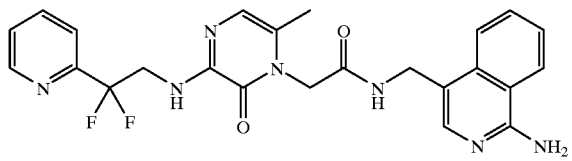

2-[3-(2-(2-pyrdyl)ethylamino)-6-methylpyrazin-2-one-1-yl]-N-(4-[(1-amino)-isoquinolinylylmethyl)]-acetamide
High resolution mass spectrum M+H=480.1950

EXAMPLE 18

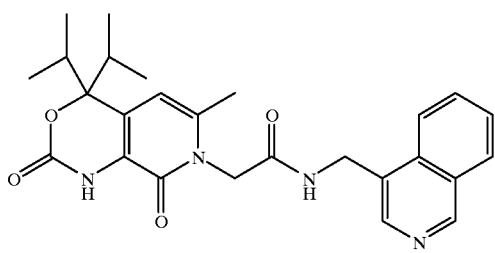

L-426,105-001P
2-(4,4-diisopropyl-6-methyl-2,8-dioxo-1,2,4,8-tetrahydropyrdo[3,4-d][1,3]oxazin-7-yl)-N-(4-isoquinolinylylmethyl)-acetamide
High resolution mass spectrum M+H=463.2320

EXAMPLE 19

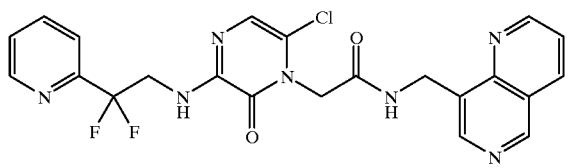

2-[3-(2,2-difluoro-2-(2-pyridyl)ethylamino)-6-chloropyrazin-2-one-1-yl]-N-(8-(16-napthydinylmethyl))-acetamide
High resolution mass spectrum M+H=486.1270

EXAMPLE 20

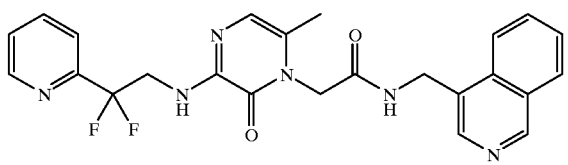

L-424,503-000V
2-[3-(2,2-difluoro-2-(2-pyridyl)ethylamino)-6-methylpyrazin-2-one-1-yl]-N-(4-isoquinolinylylmethyl)-acetamide
Electrospray mass spectrum M+H=465.2

EXAMPLE 21

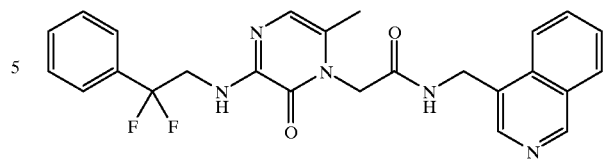

2-[3-(2,2-difluoro-2-phenethylamino)-6-methylpyrazin-2-one-1-yl]-N-(4-isoquinolinylylmethyl)-acetamide
High resolution mass spectrum M+H=464.1864

EXAMPLE 22

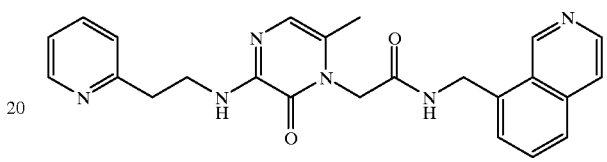

2-[3-(2-(2-pyridyl)ethylamino)-6-methylpyrazin-2-one-1-yl]-N-(8-isoquinolinylylmethyl)-acetamide
Electrospray mass spectrum M+H=429.3

EXAMPLE 23

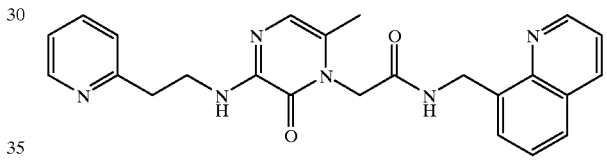

2-[3-(2-(2-pyridyl)ethylamino)-6-methylpyrazin-2-one-1-yl]-N-(8-quinolinylylmethyl)-acetamide
Electrospray mass spectrum M+H=429.3

EXAMPLE 24

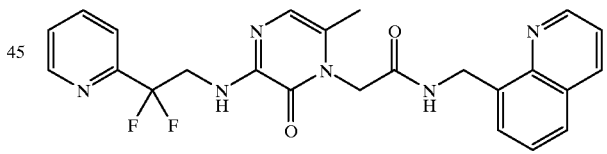

2-[3-(2,2-difluoro-2-(2-pyridyl)ethylamino)-6-methylpyrazin-2-one-1-yl]-N-(8-quinolinylylmethyl)-acetamide
High resolution mass spectrum M+H=465.1840

EXAMPLE 25

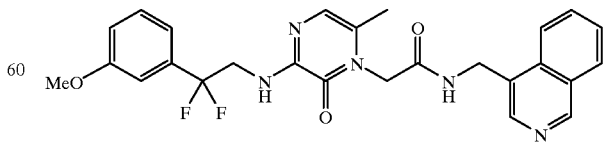

2-[3-(2,2-difluoro-2-(3-methoxyphenyl)-ethylamino)-6-methylpyrazin-2-one-1-yl]-N-(4-isoquinolinylylmethyl)-acetamide High resolution mass spectrum M+H=494.2015

EXAMPLE 26

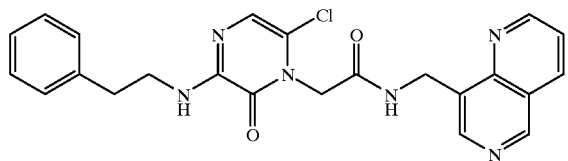

2-[3-(2-phenethylamino)-6-chloropyrazin-2-one-1-yl]-N-(8-(1,6-napthyridinylmethyl))-acetamide
High resolution mass spectrum M+H=449,1807

EXAMPLE 27

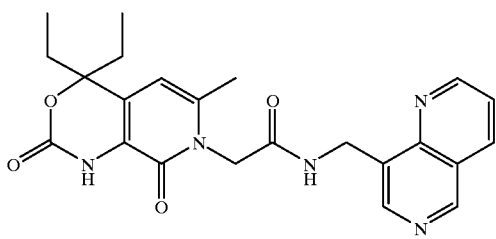

2-(4,4-diethyl-6-methyl-2,8-dioxo-1,2,4,8-tetrahydropyrido[3,4]-[1,3]oxazin-7-yl)-N-(8-(1,6-napthyridinylmethyl))-acetamide
High resolution mass spectrum M+H=436.1972

EXAMPLE 28

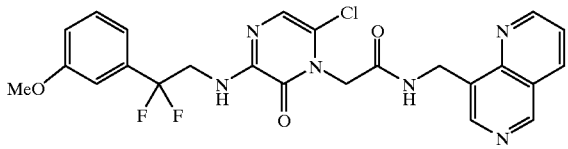

2-[3-(2,2-difluoro-2-(3-methoxyphenyl)-ethylamino)-6-chloropyrazin-2-one-1-yl]-n-(8-(1,6-napthyridinylmethyl))-acetamide
High resolution mass spectrum M+H=515.1413

What is claimed is:
1. A compound of the formula

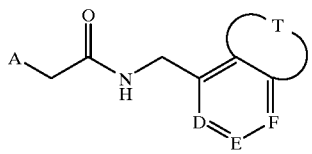

or a pharmaceutically acceptable salt thereof, wherein
T is selected from the group consisting of

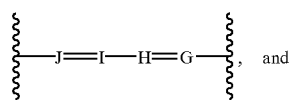, and

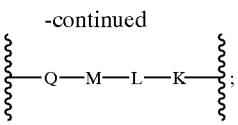;

D, E, F, G, H, I, and J are independently N or C $Y^1$, provided that the number of such variables D, E, F, G, H, I, and J representing N is 0, 1, or 2;

K, L, M and Q are independently NH or C $Y^1Y^2$, provided that the number of such variables D, E, F, K, L, M, and Q representing N is 0, 1, or 2;

$Y^1$ and $Y^2$ are independently selected from the group consisting of
hydrogen,
$C_{1-4}$ alkyl,
halogen,
amino, or
hydroxy;

A is

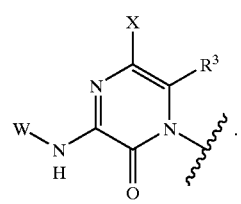

W is
hydrogen,
$R^1$,
$R^1OCO$,
$R^1CO$,
$R^1SO_2$,
$R^1(CH_2)_nNHCO$, or
$(R^1)_2CH(CH_2)_nNHCO$,
wherein n is 0–4;

$R^1$ is
$R^2$,
$R^2(CH_2)_mC(R^{12})_2$, where m is 0–3, and each $R^{12}$ can be the same or different,
$(R^2)(OR^2)CH(CH_2)_p$, where p is 1–4,

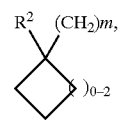

where m is 0–3,
$R^2C(R^{12})_2(CH_2)_m$, wherein m is 0–3, and each $R^{12}$ can be the same or different, wherein $(R^{12})_2$ can also form a ring with C represented by $C_{3-7}$ cycloalkyl,
$R^2CH_2C(R^{12})_2(CH_2)_q$, wherein q is 0–2, and each $R^{12}$ can be the same or different, wherein $(R^{12})_2$ can also form a ring with C represented by $C_{3-7}$ cycloalkyl,
$(R^2)_2CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicylic alkyl, $C_{10-16}$ tricylic alkyl, or a 5- to 7-membered mono- or bicyclic heterocyclic ring which can be saturated or unsaturated, and which consists of from one to three heteroatoms selected from the group consisting of N, O and S, $R^2(CH_2)_tO(CH_2)_p$, wherein t is 0 or 1 and p is 1–4,
$R^2CF_2C(R^{12})_2$,
$(R^2CH_2)(R^2CH_2)N—$,
$(R^2CH_2)(R^2CH_2)CH$, or
$R^2(COOR^3)(CH_2)r$, where r is 1–4;

$R^2$ and $R^4$ are independently
phenyl, unsubstituted or substituted with one or more of $C_{1-4}$ alkyl, $C_{1-4}$ alkoxy, halogen, hydroxy, COOH, $CONH_2$, $CH_2OH$, $CO_2R'$, where R' is $C_{1-4}$ alkyl, or $SO_2NH_2$,
naphthyl,
biphenyl,
pyridine N-oxide,
a 5- to 7-membered mono- or a 9- to 10-membered bicyclic
  a) non-heterocyclic ring system, which is saturated or unsaturated, and which is unsubstituted or substituted with halogen or hydroxy, or
  b) heterocyclic ring system, which is saturated or unsaturated, having carbon ring atoms and heteroatom ring atoms, wherein the ring system consists of i) from one to four heteroatoms selected from the group consisting of N, O, and S, and wherein the ring system is unsubstituted, or ii) from one to four nitrogen atoms, wherein one or more of the carbon and nitrogen ring atoms are substituted with halogen or hydroxy,
$C_{1-7}$ alkyl, unsubstituted or substituted with one or more of hydroxy,
COOH,
amino,
aryl,
$C_{3-7}$ cycloalkyl,
$CF_3$,
$N(CH_3)_2$,
—$C_{1-3}$alkylaryl,
heteroaryl, or
heterocycloalkyl,
$CF_3$
$C_{3-7}$ cycloalkyl, unsubstituted or substituted with aryl,
$C_{7-12}$ bicyclic alkyl, or
$C_{10-16}$ tricyclic alkyl;

$R^3$, $R^5$ and $R^6$ are independently selected from the group consisting of
hydrogen,
halogen,
$C_{1-4}$ alkyl,
$C_{3-7}$ cycloalkyl, or
trifluoromethyl;
X is
hydrogen, or
halogen;
Z is $CH_2$, S, or $SO_2$;
$R^{12}$ is
hydrogen,
phenyl, unsubstituted or substituted with one or more of $C_{1-4}$ alkyl, $C_{1-4}$ alkoxy, halogen, hydroxy, COOH, $CONH_2$,
naphthyl,
biphenyl,
a 5- to 7-membered mono- or a 9- to 10-membered bicyclic heterocyclic ring which can be saturated or unsaturated, and which consists of from one to four heteroatoms selected from the group consisting of N, O and S, $C_{1-4}$ alkyl, unsubstituted or substituted with one or more of hydroxy,
OH,
COOH,
amino,
—$N(CH_3)_2$,
—$NH(CH_3)$,
—$N(CH_2)COOH$,
aryl,
heteroaryl, or
heterocycloalkyl,
$CF_3$
$C_{3-7}$ cycloalkyl,
$C_{7-12}$ bicyclic alkyl, or
$C_{10-16}$ tricyclic alkyl.

2. A compound of claim 1, or a pharmaceutically acceptable salt therof, wherein $Y^1$ and $Y^2$ are hydrogen or amino.

3. A compound of claim 2, or a pharmaceutically acceptable salt thereof, wherein $R^5$ and $R^6$ are independently selected from —$CH(CH_3)_2$ and —$CH_2CH_3$, and W is selected from the group consisting of:

4. A compound of claim 3, or a pharmaceutically acceptable salt thereof, selected from the group consisting of

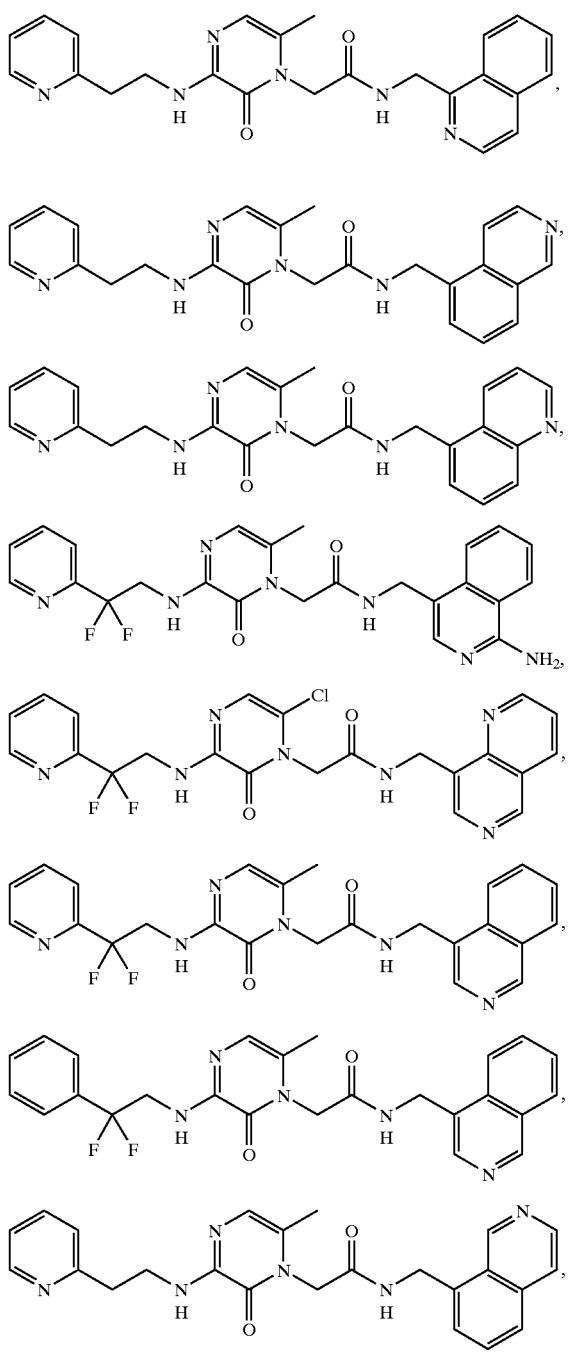
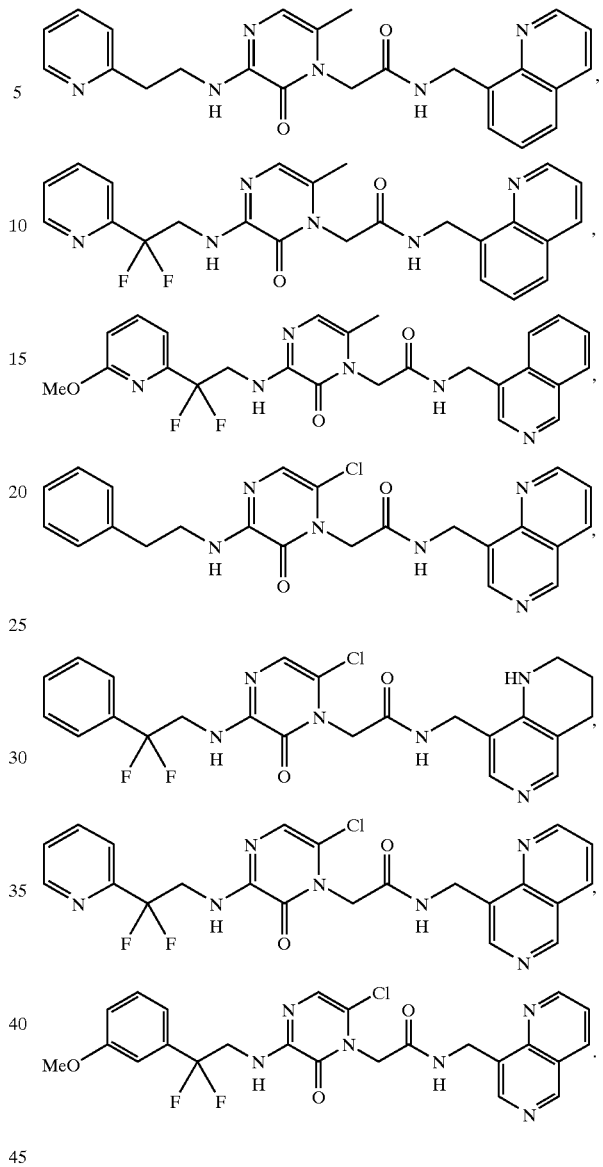
5. A composition comprising a compound of claim 1 and a pharmaceutically acceptable carrier.
6. A method for inhibiting thrombin in blood comprising adding to the blood a composition of claim 5.
7. A method for inhibiting thrombus formation in blood comprising adding to the blood a composition of claim 5.
* * * * *